(12) United States Patent  
Artero et al.

(10) Patent No.: US 8,895,207 B2  
(45) Date of Patent: Nov. 25, 2014

(54) MATERIALS AND THEIR USE FOR THE ELECTROCATALYTIC EVOLUTION OR UPTAKE OF $H_2$

(75) Inventors: Vincent Artero, Quaix en Chartruse (FR); Marc Fontecave, Saint Ismier (FR); Serge Palacin, Montigny le Bretonneux (FR); Alan Le Goff, Lannion (FR); Bruno Jousselme, Massy (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 718 days.

(21) Appl. No.: 13/125,210

(22) PCT Filed: Oct. 20, 2009

(86) PCT No.: PCT/IB2009/007333  
§ 371 (c)(1),  
(2), (4) Date: Aug. 9, 2011

(87) PCT Pub. No.: WO2010/046774  
PCT Pub. Date: Apr. 29, 2010

(65) Prior Publication Data  
US 2011/0294044 A1   Dec. 1, 2011

(30) Foreign Application Priority Data  
Oct. 21, 2008   (EP) .................................. 08290988

(51) Int. Cl.  
*H01M 4/02* (2006.01)  
*C07D 487/18* (2006.01)  
(Continued)

(52) U.S. Cl.  
CPC .............. *H01M 4/9008* (2013.01); *Y02E 60/50* (2013.01); *C07D 487/18* (2013.01);  
(Continued)

(58) Field of Classification Search  
CPC ............. B01J 31/1616; B01J 31/1625; H01M 4/9008; H01M 4/9075; H01M 4/9083  
USPC ......................................... 429/523, 530, 531  
See application file for complete search history.

(56) References Cited

U.S. PATENT DOCUMENTS 5,300,203 A   4/1994   Smalley  
5,316,636 A   5/1994   Bunshah et al.  
(Continued)

FOREIGN PATENT DOCUMENTS

EP   1 914 755 A1   4/2008  
EP   1 939 961 A1   7/2008  
(Continued)

OTHER PUBLICATIONS

Artero et al., "Some general principles for designing electrocatalysts with hydrogenase activity", Coord. Chem. Rev. 249 (2005) 1518-1535.*

(Continued)

*Primary Examiner* — Zachary Best  
(74) *Attorney, Agent, or Firm* — Alston & Bird LLP

(57) ABSTRACT

Novel materials comprising a solid support, linker arms and metal-organic complexes, and their use for the electrocatalytic production and oxidation of H2. Such materials can be used for the production of electrodes in the field of electronics, and notably electrodes for fuel cells, electrolysers and photoelectrocatalytical (PEC) devices.

14 Claims, 17 Drawing Sheets

(51) Int. Cl.

| | |
|---|---|
| *C07D 257/02* | (2006.01) |
| *C07D 471/08* | (2006.01) |
| *C25B 11/04* | (2006.01) |
| *C07D 487/22* | (2006.01) |
| *C07F 15/04* | (2006.01) |
| *H01M 4/90* | (2006.01) |
| *C07F 9/6587* | (2006.01) |
| *C07F 17/02* | (2006.01) |
| *H01M 4/86* | (2006.01) |
| *C02F 1/461* | (2006.01) |
| *C02F 101/36* | (2006.01) |

(52) U.S. Cl.
CPC .......... *C07B 2200/11* (2013.01); *C07D 257/02* (2013.01); *C07D 471/08* (2013.01); *C25B 11/0442* (2013.01); *C07D 487/22* (2013.01); *Y02E 60/523* (2013.01); *C07F 15/045* (2013.01); *C02F 2001/46133* (2013.01); *C07F 9/6587* (2013.01); *C02F 1/46109* (2013.01); *C07F 17/02* (2013.01); *C02F 2101/36* (2013.01); *C25B 11/0489* (2013.01); *H01M 4/86* (2013.01)
USPC ............ 429/531; 429/530; 429/532; 429/523

(56) References Cited

U.S. PATENT DOCUMENTS

| | | | |
|---|---|---|---|
| 5,985,232 | A | 11/1999 | Howard et al. |
| 2003/0082444 | A1* | 5/2003 | Kuhr et al. .................. 429/149 |
| 2004/0057896 | A1 | 3/2004 | Kronholm et al. |
| 2004/0202876 | A1 | 10/2004 | Kobuke et al. |
| 2005/0244644 | A1* | 11/2005 | Hampden-Smith et al. .. 428/408 |
| 2006/0058500 | A1 | 3/2006 | Bert et al. |
| 2006/0093885 | A1 | 5/2006 | Krusic et al. |
| 2006/0115712 | A1* | 6/2006 | Kim et al. .................. 429/44 |
| 2007/0248845 | A1 | 10/2007 | Armstrong et al. |
| 2008/0191202 | A1 | 8/2008 | Hobara |

FOREIGN PATENT DOCUMENTS

| | | |
|---|---|---|
| JP | 2008-12630 | 1/2008 |
| WO | WO 92/04279 | 3/1992 |
| WO | WO 03/019705 A2 | 3/2003 |
| WO | WO 2004/114494 A2 | 12/2004 |
| WO | WO 2006/063992 A2 | 6/2006 |
| WO | WO 2006/074829 A1 | 7/2006 |

OTHER PUBLICATIONS

Search Report and Written Opinion for International Application No. PCT/IB2009/007333, mailed Dec. 29, 2009.
Artero, V., et al.; "Some general principles for designing electrocatalysts with hydrogenase activity"; Coordination Chemistry Reviews; Aug. 2005; vol. 249; Issues 15-16; pp. 1518-1535.
Kellett, R., et al.; "Cobalt Porphyrin Electrode Films as $H_2$ Evolution Catalysts"; Inorganic Chemistry; Jul. 1985; vol. 24, Issue 15; pp. 2378-2382.
Nikolaev, P., et al.; "Gas-phase catalytic growth of single-walled carbon nanotubes from carbon monoxide"; Chemical Physical Letters 313; Nov. 1999; pp. 91-97.
Trancik, J.C., et al.; "Transparent and Catalytic Carbon Nanotube Films"; NANO Letters; Jan. 2008; vol. 8, Issue 4; pp. 982-987.
Vijaikanth, V., et al.; "Chemically modified electrode based on an organometallic model of the [FeFe] hydrogenase active center"; Electrochemistry Communications; Apr. 2005; vol. 7, Issue 4; pp. 427-430.

\* cited by examiner

Scheme 1

Scheme 2

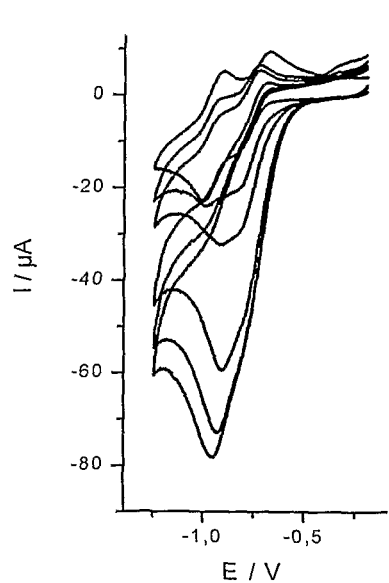
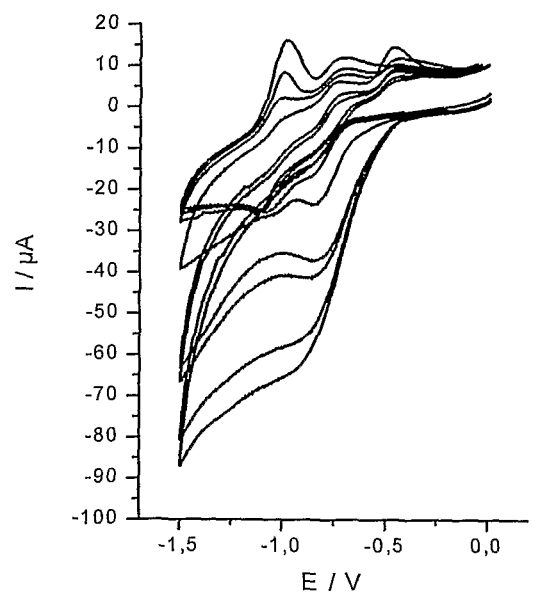
Figure 5a
Figure 5b
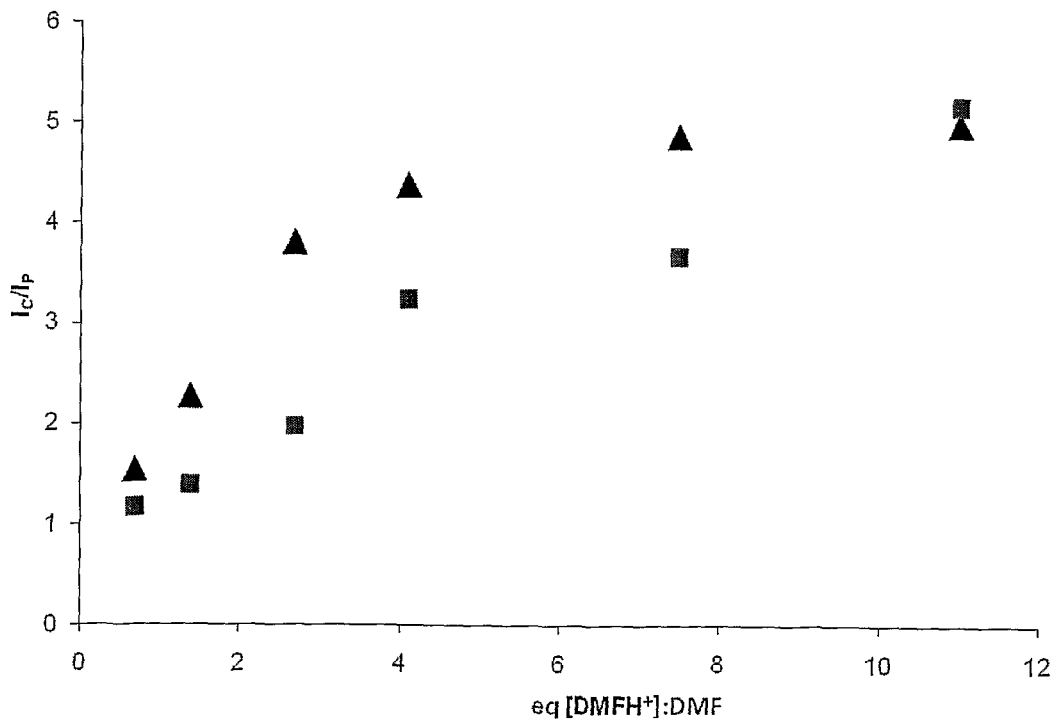
Figure 6

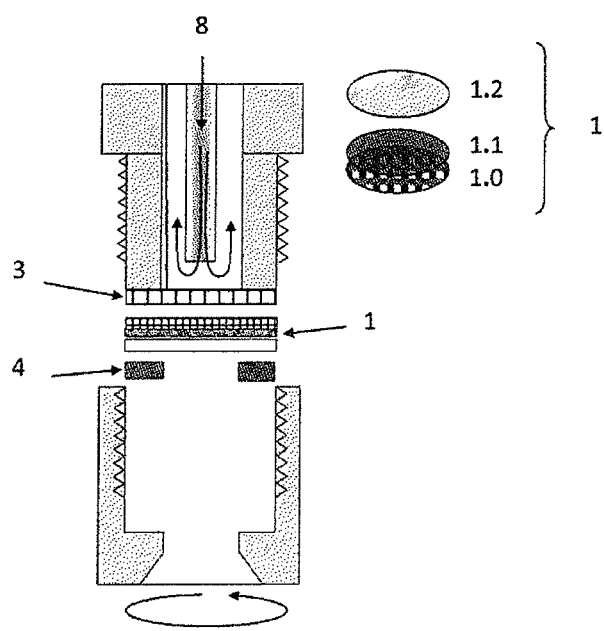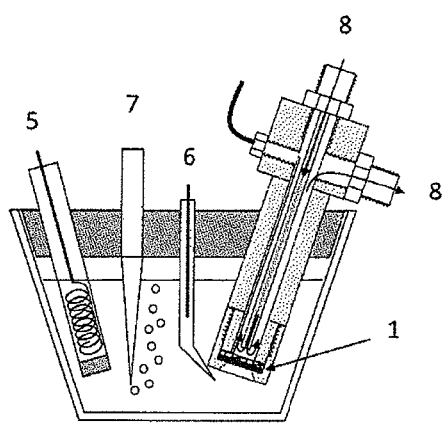
Figure 18A
Figure 18B

MATERIALS AND THEIR USE FOR THE ELECTROCATALYTIC EVOLUTION OR UPTAKE OF H$_2$

FIELD OF THE INVENTION

The invention is directed to novel materials and their use for the electrocatalytic production and oxidation of H$_2$. More particularly, it concerns materials which can be used for the production of electrodes in the field of electronics, and notably electrodes for fuel cells, electrolysers and photoelectrocatalytical (PEC) devices.

BACKGROUND OF THE INVENTION

Molecular hydrogen is widely considered as a convenient energy vector. Its combustion in a fuel cell generates electricity with high yield and without any pollutant exhaust, water being the sole reaction product. However, although hydrogen is one of the most abundant elements on earth, molecular hydrogen exists only as traces in the atmosphere and has to be produced through processes that require some energy input. Thus the economically viable production of H$_2$ from renewable sources is a major concern to the scientific community. Electrolysis (reduction of proton into H$_2$ by mean of electrical energy) or photoelectrolysis (reduction of proton into H$_2$ by mean of light energy sometimes with additional electrical energy) is one way to produce H$_2$ from water (or a convenient proton source). Reduction of protons is apparently a very simple reaction. Unfortunately, it progresses slowly on most electrodes except on noble metals such as platinum. Hence hydrogen evolution is generally not observed at potentials near equilibrium (−400 mV vs. SHE at pH 7 in water) but requires the application of an overpotential also called activation potential. The same occurs for hydrogen oxidation. This kinetic limitation thus significantly reduces the energetic yield during a complete formation/uptake cycle of hydrogen and is therefore economically limiting for most industrial applications.

Fuel cells are electrochemical devices that convert the energy of a fuel directly into electrical and thermal energy. Generally, a fuel cell consists of an anode and a cathode, separated by an electrolyte through which they are electrically connected. A fuel, usually hydrogen, is fed to the anode where it is oxidised with the help of an electrocatalyst. At the cathode, the reduction of an oxidant such as oxygen, and usually air, takes place. The electrochemical reactions at the electrodes produce an electrical current and therefore produce electrical energy. Usually, thermal energy is also produced in parallel and can be used to provide additional electricity or for other purposes.

Currently the most common electrochemical reaction which is performed in a fuel cell is the reaction between hydrogen and oxygen to produce water. Molecular hydrogen may be fed to the anode where it is oxidised, the electrons produced passing through an external circuit to the cathode where the oxidant is reduced. Ions flowing through the intermediate electrolyte maintain charge neutrality. Fuel cells can be adapted to use other fuels such as methanol, hydrazine or natural gas.

Water electrolysers are made as fuel cells but are operated the reverse, with the application of electrical power between the electrodes and supply with water. Hydrogen is generated at the cathode and oxygen is generated at the anode.

Various difficulties have prevented the commercial development of fuel cell and water electrolyser technologies. The first one is cost and, in particular, the cost of the electrocatalysts employed at both the cathode and the anode to facilitate the electrochemical interconversion of $2H^+ + 2e^-$ into H$_2$ in the most versatile technology based on proton exchange membrane such as Nafion ®. The most commonly used electrocatalyst is platinum. Platinum is a very efficient catalyst and enables high currents to be produced in the fuel cell. However, its cost is high, and platinum is of limited availability. Therefore the metal catalyst is a significant contributor to the expense of the fuel cell. A further difficulty is that platinum is available in limited quantities on earth and world supplies cannot be expected to last more than a few decades if the use of fuel cells was to be generalized, in cars notably (Gordon et al. Proc. Natl Acas Sci USA, 2006, 1209-1214). The active layers for either hydrogen electro-evolution or electro-oxidation contain nanoparticles of Pt or other noble metals coated onto a carbon material: Pt nanoparticle catalysts stem from mid 20$^{th}$ century research on chemical catalysis in the gas phase and have been largely optimized up to now. While this solution is today the sole which is economically viable, nanoparticles (usually with a diameter of 5 nm and more) present no more than 10% of their atoms on their surface, while 90% of metal weight is unnecessarily immobilised, resulting in a cost/efficiency unfavourable balance.

Another difficulty with platinum comes from the fact that it is irreversibly inactivated in the presence of carbon monoxide. Many sources of hydrogen gas contain carbon monoxide impurities. The use of platinum catalysts therefore requires hydrogen fuel of high purity, with extremely low carbon monoxide levels. This adds to the cost of operating the fuel cell.

As a consequence, the existence of a global hydrogen economy appears to be dependent upon the development of new base-metal catalysts for hydrogen production and uptake.

Alternatives to platinum catalysts have been the object of numerous studies: one possibility is the use of hydrogenase enzymes at the anode. Electrodes based on the combination of hydrogenase enzymes with a carbon material have been disclosed in WO 2003/019705 ; US 2007/0248845 ; EP1939961 ; WO2004/114494, and more extensively in J. A. Cracknell et al., Chem. Rev. 2008, 108, 2439-2461. However, hydrogenases have been found to be highly sensitive to the presence of oxygen, and become inactive over a period of time when used in a standard fuel cell operating with oxygen (or an oxygen containing material such as air) as the oxidant. Moreover, they are very difficult to produce in a catalytically active form in significant amounts. A representative preparation requires two weeks for a few milligrams of enzymes corresponding to a few amount of active molecule since the molecular weight of the catalyst is about 55 kg.mol$^{-1}$.

US2006/0093885 discloses functionalized carbon materials which can be used in electrochemical assemblies for electrochemical cells or fuel cells. But the catalyst is based on noble metal particles dispersed in a polymer.

WO2006063992 and US2006/0058500 disclose metal particles formed from a polymeric resin, a transition metal and a reducing agent and their use to make electrodes for fuel cells.

WO2006074829 discloses metal-organic complexes which are used as a coating on an anion conducting membrane, further reduced to form metal particle and fuel cells made from such membranes.

In these three last documents, metal ions are reduced to form nanoparticles and catalytic activity relies on the use of these nanoparticles.

The immobilization of metal-organic complexes on the surface of electrodes has also been achieved with the same aim: Kellet, R. M. and Spiro, T. G., (Inorg. Chem. 1985, 24, 2378) reported a series of cobalt porphyrins with high activity for $H_2$ production, associated with low overvoltage in neutral aqueous solution. However, these compounds proved difficult to handle when covalently grafted to an electrode via an amide link with surface carboxylic acid groups: film instability or disrupting processes at either film-electrode or film-electrolyte interfaces were postulated. In another example, incorporating positively charged cobalt porphyrin complexes into a Nafion ® membrane coated on a glassy carbon electrode resulted in low electroactivity, reflecting the poor electron-transfer characteristics of Nafion ® films. T. Abe et al. (Polym. Adv. Technol. 1998, 9, 559) reported that cobalt tetraphenylporphyrin incorporated in a Nafion ® membrane coated on a bare pyrolytic graphite electrode can reduce protons only with a larger overvoltage (−0.7 V vs Ag/AgCl) in a pH 1 aqueous solution together with a considerably lower 70 $h^{-1}$ turnover frequency value. Better turnover frequency ($2.10^5$ $h^{-1}$) was observed but still with a large overvoltage at a potential of −0.90 vs Ag/AgCl and pH=1 for a cobalt phthalocyanine incorporated in a poly(4-vinylpyridine-co-styrene) film coated on a graphite electrode. In that case again the catalytic proton reduction was limited by the electron transfer within the matrix (Zhao et al. J. Mol. Catal. A 1999, 145, 245). Electropolymerization of $[Cp*Rh(L)Cl](BF_4)$ (L=bis-4,4'-bispyrrol-1-ylmethypmethoxycarbonyl]-2,2'-bipyridyl) leads to a stable film capable of proton electroreduction. Quantitative current efficiency corresponding to 353 turnovers was observed during a 14 hours electrolysis experiment at pH 1 using a carbon-felt electrode coated with the electropolymerized rhodium complex. Here again, turnover frequency is low and overvoltage dominates (Cosnier et al. J. Chem. Soc. Chem. Comm. 1989, 1259). More recently, the immobilization of diiron complexes (also known to be molecular electrocatalysts for hydrogen evolution) on carbon materials, either via the eleetropolymerisation of diazonium salts on glassy carbon (V. Vijaikanth et al. Electrochemistry communication, 2005, 7, 427-430) or via polypyrrole coating (S. K. Ibrahim et al. Chem Commun 2007, 1535-1537) has been described. However, although diiron complexes in solution show promising. electrocatalytic activity, there is little or no activity retained after grafting.

Document EP-1 914 755 discloses nanoscale electrochemical cell arrays wherein each cell comprises a well. A wall of the well comprises at least one electrode. Molecules can be coupled to the electrode via a linker. Organometallic complexes covalently or ionically linked to an electrode are disclosed. However such grafting provides surfaces which retain little or no catalytic activity.

Document US2004/0202876 discloses photofunctional molecules consisting of porphyrins oligomers or polymers covalently grafted to a substrate. However such complexes retain little or no catalytic activity.

Today, there are no viable solutions to efficiently replace platinum as electrocatalyst at the anode of a hydrogen fuel cell.

SUMMARY OF THE INVENTION

It has been an aim of this invention to provide a solution to the problems of the prior art, and notably: to provide a material which can be used as electrocatalyst in fuel cells and electrolysers, which is easy to prepare, based on cheap materials, and permits the economically viable production and oxidation of $H_2$, which implies a catalyst with a low activation potential, and a resistance to degradation under working conditions.

The solution to this problem is a new material comprising a classical electrode solid support, on which a coordination complex is grafted through a linker arm.

It has been found that, in the material of the invention, metal-organic complexes retained their electrocatalytic activity once grafted on the solid support thanks to the use of selected linkers. Furthermore, the immobilization, when carried out via this procedure, does not result in an increased overvoltage as compared to that observed for the catalyst in solution. Materials of the invention differ from prior art materials showing little or no catalytic activity notably by the nature of the linker arm.

The material of the invention is easy to prepare, can be integrated in a fuel cell or in an electrolyser as an electrode. It works as molecular electrocatalyst for hydrogen evolution or oxidation, and is characterized by an improved stability (characterized by the total number of catalytic cycles achieved). In addition, the catalytic layer can be made transparent so that it can be used as cathode in a photoelectrocatalytical device.

A first object of the invention is a material comprising a solid support of a conductive or semi-conductive material which is functionalized on its surface by linker arms, said linker arms comprising at least two extremities, wherein the first extremity is bonded to the solid support either by a covalent link or via π-stacking interaction and the second extremity is linked in a covalent manner to a metal-organic complex (C*). Such a material is schematically illustrated on schema A here-under.

Scheme A

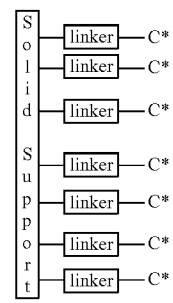

The solid support preferably has the shape of a plaque, but this shape can be different. Notably, the solid support can have the shape of a rod, a cylinder or wire, according to the device in which it is used.

The solid support advantageously is a conductive or semi-conductive material with a high specific surface. It may be nano-structured or not. This conductive or semi-conductive material with a high specific surface may be deposited on another support of a conductive material, in order to form an electrode with a high specific surface. This other conductive material may be made of any conducting material, for example indium tin oxide (ITO), stainless steel, iron, copper, nickel, cobalt, aluminium (in particular when it is freshly brushed), gold, doped-diamond, titanium, brass or carbon, e.g. graphite. Preferably it is made of a material selected from ITO and graphite.

Materials for the preparation of the solid support can be selected from: a metallic material, a carbon material, a semi-conductor or conductor metal oxide, nitride or chalcogenide.

When the solid support is a metallic material, it can be selected from: silicon, brass, stainless steel, iron, copper, nickel, cobalt, aluminium (in particular when it is freshly brushed), silver, gold or titanium.

Functionalisation on a metallic solid support is performed by a reaction with an aryl radical from the linker molecule leading to covalent grafting.

When the solid support is a carbon material, it can be selected from:
- a curved carbon nanostructure like carbon black, single or multi-walled carbon nanotubes (CNT), fullerenic nanoparticles,
- graphite,
- glassy carbon (expanded or not, or a foam),
- graphene,
- doped diamond, A curved carbon nanostructure includes, but is not limited to, a carbon nanotube (CNT), a fullerenic nanoparticle and carbon black.

Methods for the preparation of CNT include laser vaporization of graphite (Thess et al, Science 273, 1996, 483), arc discharge (Journet et al, Nature 388, 1997, 756) and the HiPCo (high pressure carbon monoxide) process (Nikolaev et al, Chem. Phys. Lett. 313, 1999, 91-97). Other methods for producing CNTs include chemical vapor deposition (Kong et al, Chem. Phys. Lett. 292, 1998, 567-574; Cassell et al, J. Phys. Chem. 103, 1999, 6484-6492); and catalytic processes both in solution and on solid substrates (Yan Li et al, Chem. Mater. 13(3); 2001, 1008-1014 ; A. Cassell et al, J. Am. Chem. Soc. 121, 1999, 7975-7976).

Methods for preparing fullerenic nanoparticles are described in U.S. Pat. No. 5,985,232 and US 2004/057,896. Fullerenic nanoparticles are available commercially from suppliers such as Nano-C Corporation, Westwood Mass.

Carbon black is a powdered form of highly dispersed, amorphous elemental carbon. It is a finely divided, colloidal material in the form of spheres and their fused aggregates. Different types of carbon black can be distinguished by the size distribution of the primary particles, and the degree of their aggregation and agglomeration.

Carbon black is made by a method selected from controlled vapor-phase pyrolysis and/or thermal cracking of hydrocarbon mixtures such as heavy petroleum distillates and residual oils, coal-tar products, natural gas and acetylene. Acetylene black is the type of carbon black obtained by the burning of acetylene. Channel black is made by impinging gas flames against steel plates or channel irons, from which the deposit is scraped at intervals. Furnace black is the name of carbon black made in a refractory-lined furnace. Lamp black is made by burning heavy oils or other carbonaceous materials in closed systems equipped with settling chambers for collecting the solids. Thermal black is produced by passing natural gas through a heated brick checkerwork where it thermally cracks to form a relatively coarse carbon black. Carbon black is available commercially from many suppliers such as Cabot Corp.

A fullerene is a spherical allotrope of carbon. It is a molecule composed entirely of an even number of carbon atoms in the $sp^2$-hybridized state and takes the form of a closed cage. The most abundant species is the C60 molecule, and the second most abundant species of the fullerene family is C70. Fullerenes include not only single-walled but also multi-walled cages consisting of stacked or parallel layers. The preparation of fullerenes has been disclosed notably in WO 92/04279, U.S. Pat. Nos. 5,316,636, 5,300,203, and Howard et al., Nature 352, 1991, 139-141. Fullerenes may be obtained commercially from suppliers such as Carbon Nanotechnologies Incorporated, MER Corporation, Nano-C Corporation, TDA Research Inc., Fullerene International Corp., and Luna Innovations.

In order to be functionalized, carbon materials used in this invention include carbon materials having unsaturations (graphite, graphene, carbon nanotubes, carbon black, glassy carbon): They are functionalized in a known manner:
- by addition chemistry performed on one or more C=C double bonds at the surface. Aryl radicals, generated by reduction of diazonium salts from linker arm precursors, interact with carbon material in this way.
- via π-stacking interaction of graphene layers of the carbon materials with aromatic moieties of the linker arms such as phenyl, biphenyl, anthracene, pyrene, perylene, and other polyaromatic groups.

When the solid support is a semi-conductor or conductor metal oxide, nitride or chalcogenide, it can be selected from: $TiO_2$, $NiO$, $ZnO$, $ZrO_2$ ITO, $SnO_2$, $WO_3$, $Fe_2O_3$, $Ta_2O_5$, $Ta_3N_5$, TaON, N-doped $TiO_2$, ZnS, ZnSe, CdS, CdSe, CdTe, ZnTe and composites of these materials, also possibly doped with other elements. Favourite metal oxide is selected from: NiO, $TiO_2$, ZnO.

Functionalization of the solid support in that case is performed by a reaction/interaction such as: a covalent link between an aryl radical of the linker molecule with the metal oxide materials.

Favourite material for the solid support is selected from: multi-wall carbon nanotubes (MWCNT), and metal oxide. Even more preferably, the solid support is selected from multi-wall carbon nanotubes (MWCNT).

The linker arms comprise at least two extremities: the first extremity is bonded to the solid support either by a covalent link or via π-stacking interaction and the second extremity is linked in a covalent manner to a metal-organic complex.

The linker should advantageously be long enough to let the molecular compound adopt the conformation required for catalysis. And preferably, the linker should be not too long, in order to avoid its forming an insulating layer at the surface of the conductive or semi-conductive material and hinder the electron transfer from the electrode to the catalyst.

Said linker arm comprises a first extremity which is bonded to the solid support in a manner that insures good electronic transfer with low resistivity and the second extremity is linked in a covalent manner to a metal-organic complex. Good electronic transfer between the solid support and the metal-organic complex can be assessed via the measurement of the electric resistivity of the layer. Low resistivity is achieved thanks to covalent linkage or π-stacking interactions between the linker and the solid support.

The linker can be selected from hydrocarbon molecules, said hydrocarbon molecule comprising at least one covalent link with the solid support or one group interacting through π-stacking with the solid support, and comprising also at least one covalent link with the metal-organic complex.

This hydrocarbon molecule is selected from those responding to the following formulae:

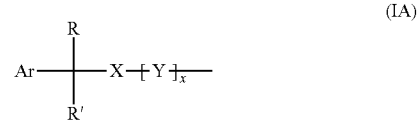

(IA)

and to oligomers resulting from the reductive oligomerization of:

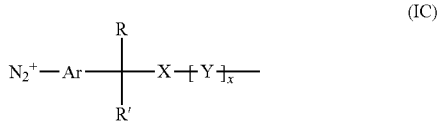

wherein:

Ar represents a $C_6$-$C_{30}$ aromatic residue, possibly comprising one or more substituants selected from: $C_1$-$C_6$ alkyl, —OH, —NH$_2$, —COOH, —F, —Cl, —Br, —I, —NO$_2$, —CONR"$_2$, —COOR", —SO$_3^-$, —SR", —OR", —NR"$_2$;

R and R', identical or different, represent a group selected from : H, $C_1$-$C_{20}$ alkyl, $C_1$-$C_{20}$ alkenyl, $C_1$-$C_{20}$ alkynyl, $C_6$-$C_{30}$ aryl, $C_6$-$C_{30}$ aralkyl, possibly comprising one or more substituants selected from: —OH, —NH$_2$, —COOH, —CONH$_2$, triazole, —SH, —N$_3$, and possibly interrupted by one or more bridges selected from: —CONH—, —CO—O—, —CO—O—CO—, —CO—NH—CO—, —CO—S—, —CS—O—, —CS—S—;

R" represents a group selected from: H, $C_1$-$C_{20}$ alkyl, $C_1$-$C_{20}$ alkenyl, $C_1$-$C_{20}$ alkynyl, $C_6$-$C_{30}$ aryl, $C_6$-$C_{30}$ aralkyl;

X represents a group selected from: $C_1$-$C_{20}$ alkyl, $C_1$-$C_{20}$, alkenyl, $C_1$-$C_{20}$ alkynyl, $C_6$-$C_{30}$ aryl, $C_6$-$C_{30}$ aralkyl, possibly comprising one or more substituants selected from: —OH, —NH$_2$, —COOH, —CONH$_2$, triazole, —SH, —N$_3$, and possibly interrupted by one or more bridges selected from: —CONH—, —CO—O—, —CO—O—CO—, —CO—NH—CO—, —CO—S—, 13 CS—O—, —CS—S—;

x is an integer, $1 \le x \le 5$, x is the number of functional groups Y which are grafted on the X group;

Y is a functional group selected from: a simple covalent link, —O—, —NH—, —S—, —COO—, —CONH—, —CO—S—, —CS—O—, —CS—S—.

Favourite linker arms are those resulting from the oligomerization of

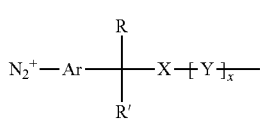

When the linker is

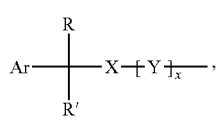

the interaction between the linker and the solid support is via π-stacking.

When the linker is an oligomer resulting from the reductive oligomerization of:

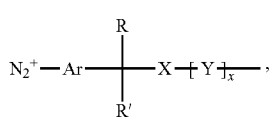

the linker is covalently linked through the Ar group, to the solid support.

In formulae (IA) and (IC), the favourite variants are the following:

Ar advantageously represents a $C_6$-$C_{30}$ aromatic residue. Ar can be selected from the following list: phenyl, biphenyl, pyrenyl, anthracenyl, phenanthrenyl, perylenyl, naphtacenyl.

Preferably R and R' represent a group selected from: H, $C_1$-$C_{20}$ alkyl, $C_1$-$C_{20}$ alkenyl, $C_1$-$C_{20}$ alkynyl, $C_6$-$C_{30}$ aryl, $C_6$-$C_{30}$ aralkyl, and even more preferably selected from: H, $C_1$-$C_{12}$ alkyl. Advantageously R=R'=H.

Preferably X represents a group selected from: $C_1$-$C_{20}$ alkyl, $C_1$-$C_{20}$ alkenyl, $C_1$-$C_{20}$ alkynyl, $C_6$-$C_{30}$ aryl, $C_6$-$C_{30}$ aralkyl. Even more preferably X represents a group selected from: $C_1$-$C_{12}$ alkyl, $C_1$-$C_{12}$ alkenyl, $C_1$-$C_{12}$ alkynyl, $C_6$-$C_{20}$ aryl, $C_6$-$C_{20}$ aralkyl.

Preferably $1 \le x \le 3$, even more preferably

Alkyl, alkenyl and alkynyl groups can be linear, branched or cyclic.

Said linker molecule can take different shapes: it can be simply a linear chain linking the solid support and the metal-organic complex, but it can also be a branched molecule comprising several arms, one or several arms being linked to the solid support and one or several arms being linked to the metal-organic complex, While other arms can remain free. This last case is especially illustrated in the experimental part wherein the linker is an oligomer resulting from the reductive oligomerization of:

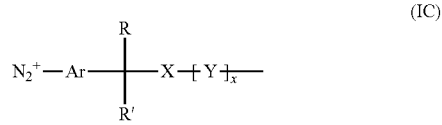

The linker is not exclusively a definite compound. During oligomerization a N$_2$ molecule can by eliminated for each (IC) molecule. During fabrication, some oligomerization of the linker can occur but this process has to be controlled in order to avoid the formation of an insulating layer between the electrode and the molecular catalyst. Several different linkers can be grafted on the same solid support and/or linked to identical metal-organic complexes. One linker arm can also be anchored to the solid support by two distinct functional groups. One linker arm can also bear more than one metal-organic complex, and those metal-organic complexes can be identical or different. Such variations are illustrated on the scheme B and C here-under:

Scheme B

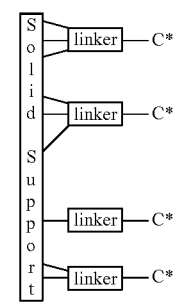

Scheme C

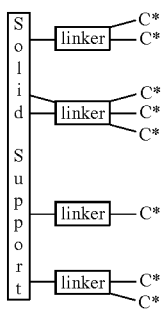

The metal-organic complex which can be used in the material of the invention is selected from those responding to the following criteria:

The metal-organic complex is a molecule comprising one or several, preferably 1, 2 or 3 metal atoms and a ligand. The metal atoms are selected from the transition metals, and especially atoms 21 to 29, 42, 44 to 46 and 74 to 78 of the periodic classification of elements and an organic ligand. Those favourite transition metal atoms are: Sc, Ti, V, Cr, Mn, Fe, Co, Ni, Cu, Mo, Ru, Rh, Pd, W, Re, Os, Ir, Pt. The ligand can be constituted of one or several distinct molecules. The metal-organic complex, when studied in solution, before grafting on the linker, displays electrocatalytic activity for hydrogen evolution or uptake. This can be assessed simply by recording cyclic voltamograms in the solvent of interest in the presence of increasing amounts of a proton source (an acid with a strength comparable to that used in the aimed application) and observing current enhancements either cathodic for hydrogen evolution or anodic for hydrogen uptake, for overpotentials (related to the equilibrium potential of the $H^+/H_2$ couple under the operating conditions) lower than 800 mV.

Preferably, electrocatalysis should rely on a reversible, pseudo-reversible or at least chemically reversible electrochemical process for the catalysts in an active state along the catalytic cycle. The metal-organic complex can be mono or polynuclear preferably with chelating, multidentate ligands for insuring stability of the coordination sphere. It is preferable for the coordination sphere of the metal not to contain a labile ligand or a ligand required for efficient catalytic properties that can be easily removed upon reduction or oxidation.

The metal-organic complex which can be used in the material of the invention could be selected from those, not limitating, responding to the following formulaes. More examples can be found in Coord. Chem. Rev. 2005 249, or Comptes Rendus Chimie 2008, 11, 8, two special issues devoted to hydrogenases and model compounds.

Metal dioxime/diimine complexes such as those having the following formulaes:

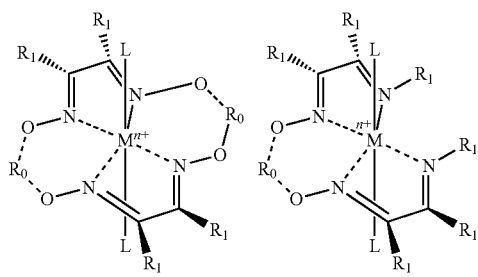

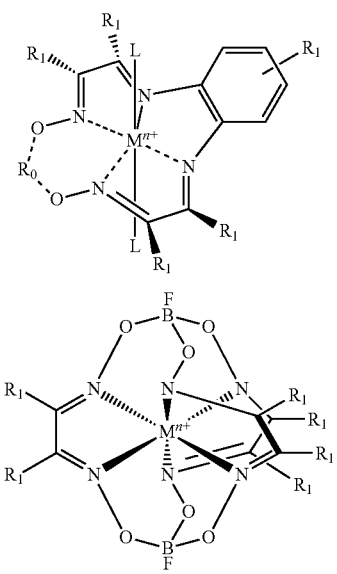

Metal amine/imine/pyridine complexes such as those having the following formulaes:

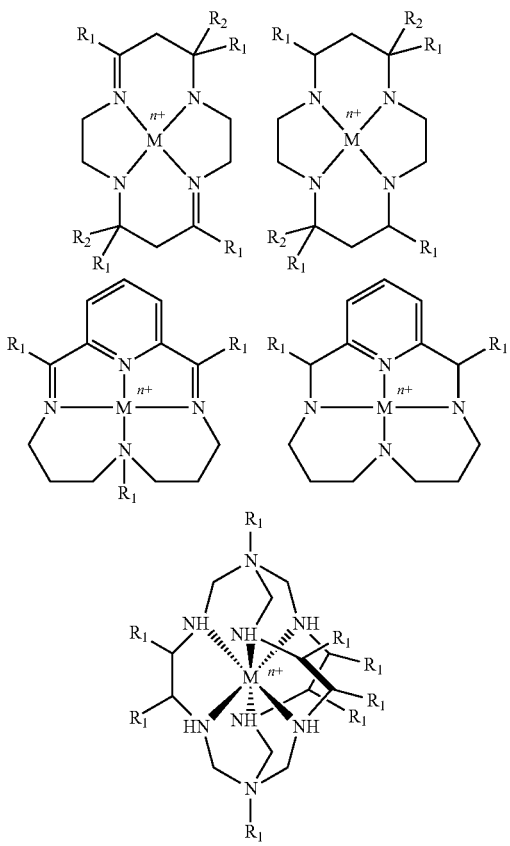

Metal porphyrins and related (extended or restricted) polypyrrole macrocycles or metal phthalocyanine complexes or metal cyclam and related polyazamacrocyclic complexes such as those having the following formulaes:

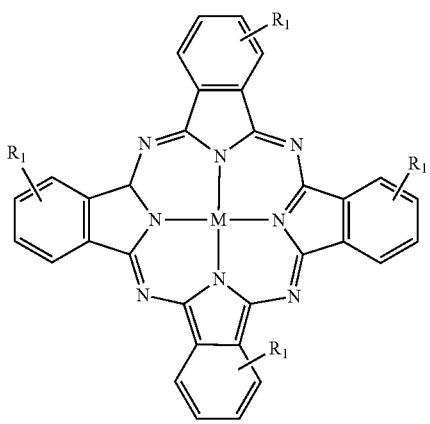

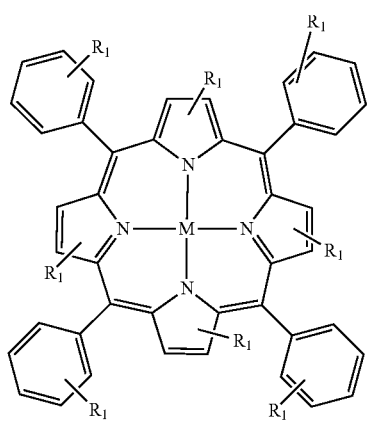

Ferrocenophane and related complexes such as those having the following formulaes

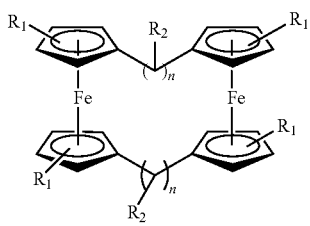

Metal diphosphine or diphosphite complexes such as those having the following formulaes:

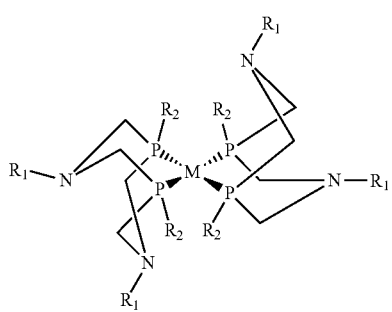

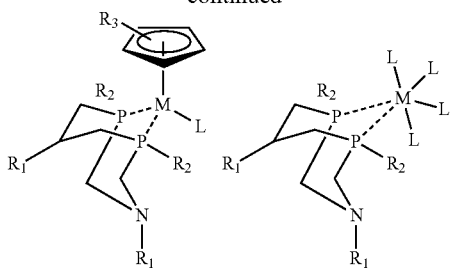

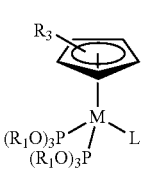

wherein

M represents an atom selected from transition metals of the periodic table of elements, and preferably, from the list which has been given above, and even more preferably M is selected from: Mn, Fe, Co, Ni, W, Mo, and advantageously M is selected from: Ni and Co.

$R_0$, identical or different, represents a group selected from H, $BF_2$, $BPh_2$, $B(R_1)_2$, $B(OR_1)_2$, $BFR_1$.

L is selected from a solvent molecule such as water, acetone methanol, ethanol, n-propanol, isopropanol, n-butanol, acetonitrile, tetrahydrofurane, dimethylformamide, dimethylsulfoxide, pyridine, an anionic ligand such as a halogen, a pseudohalogen such as SCN- or cyanide, hydride, oxygenated anion such as nitrate, sulphate, sulfonate, perchlorate, or a common monodentate ligand such as pyridine, imidazole, triazole, CO, $H_2$, formyl, phosphine, nitrile or isonitrile ligands, such as acetonitrile, benzonitrile, trimethyl isonitrile, benzylisonitrile.

n is a number comprised between 0 and 6.

$R_1$, $R_2$, $R_3$, identical or different, represent a group selected from: H, $C_1$-$C_{20}$ alkyl, $C_1$-$C_{20}$ alkenyl, $C_1$-$C_{20}$ alkynyl, $C_6$-$C_{30}$ aryl, $C_6$-$C_{30}$ aralkyl, possibly comprising one or more functions selected from: —OH, —$NH_2$, —COOH, —$CONH_2$, a triazole ring, possibly comprising one or more bridges selected from: —CO—O—CO—, —CO—NH—CO— and at least one of the $R_1$ groups, one of the $R_2$ groups or the $R_3$ group represents a covalent link with the linker molecule, two or more $R_1$ substituents can be fused together, two or more $R_2$ substituents can be fused together.

Preferably all the $R_1$ groups are identical with the possible exception of at least one $R_1$ group which is a covalent link with the linker molecule.

Preferably all the $R_2$ are identical with the possible exception of at least one $R_2$ group which is a covalent link with the linker molecule.

Preferably, the metal-organic complex is selected from metal diphosphine or diphosphite complexes such as those having the following formulaes, wherein $R_1$, $R_2$ and $R_3$ have the same definition as above:

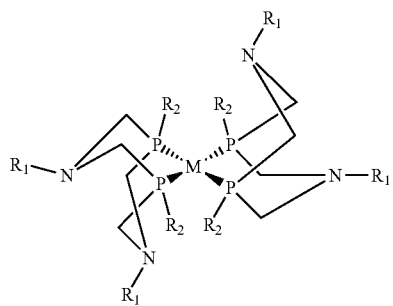

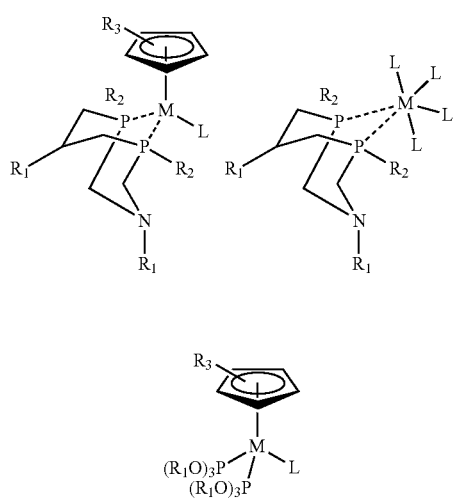

A favourite variant is with the metal-organic complex selected from those which respond to the following formula (II):

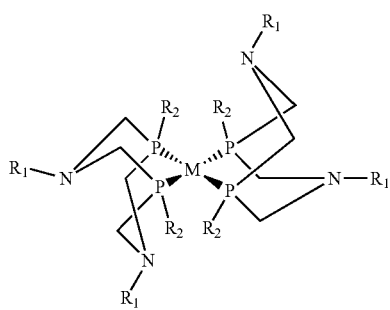
(II)

Wherein $R_1$ and $R_2$ have the same definition as above.

Advantageously all the $R_1$ are identical and represent a group selected from:

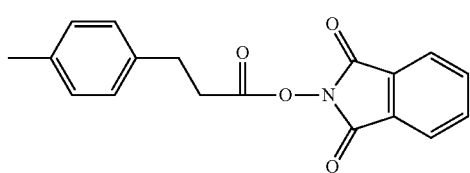

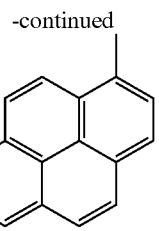

with the exception of at least one $R_1$ group which is a covalent link with the linker molecule.

Preferably, all the $R_2$ are identical and represent a phenyl group.

The functionalization of the solid support by the metal organic complex through linker arms can be done by several ways:

(i) the metal-organic complex can be first coupled with the linker and this assembly can be grafted on the conductive or semi-conductive material with a high specific surface;

(ii) the conductive or semi-conductive material with a high specific surface can be first functionalized with the linker and the metal-organic complex can be coupled afterwards on the linker using classical organic coupling reactions including methods of click chemistry;

(iii) the conductive or semi-conductive material with a high specific surface can be first functionalized with a linker already coupled with the ligand which is part of the metal-organic complex. Then the complex is formed by reacting this grafted ligand with a mixture of metal salts or metallic precursors of the complex and free ligands.

Some of these methods are illustrated in the experimental part.

When the linker is

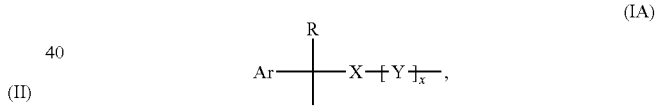
(IA)

the interaction between the linker and the solid support is via π-stacking. The linker is put in contact with the solid support and an interaction between the aryl group of the linker and the solid support is established. The linker may have been grafted or not, prior to this step, by the metal-organic complex C*, or by the ligand forming part of the metal-organic complex.

One example of the preparation of a material according to the invention, in the case wherein the linker is an oligomer resulting from the oligomerization of (IC), is illustrated on FIG. 14:

A solid support, like a carbon nanotube support (CNT), is functionalized in a first step with a linker by oligomerization of

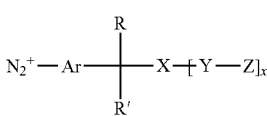

wherein Ar, X, Y, R, R' and x have the same meaning as above, and Z is a reactive group. This functionalisation results in a covalent link between the solid support and the oligomer.

Then the functionalized solid support is reacted with the metal-organic complex derivative C*W, wherein C* is the metal-organic complex and W is a reactive group able to react with Z to form a covalent link.

Another schematic representation of the preparation of a material according to the invention is illustrated on FIG. 15:

A solid support is functionalized in a first step with a linker by oligomerization of

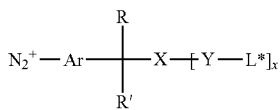

wherein Ar, X, Y, R, R' and x have the same meaning as above, and L* is the ligand or part of the ligand of the metal-organic complex. This functionalization results in a covalent link between the solid support and the oligomer. Then the functionalized solid support is reacted with the metal atom M, so that the metal atom M and its ligand L* join to form the metal organic complex C*.

Another schematic representation of the preparation of a material according to the invention is illustrated on FIG. 16:

In a first step, a linker precursor

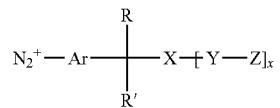

is functionalized by grafting of a metal-organic complex C* through reaction with the derivative C*W, wherein Ar, R, R', X, Y and x have the same meaning as above and W and Z represent reactive groups capable of forming together a covalent link.

A solid support is then functionalized with the linker-C* molecule resulting in oligomerization of the linker and establishment of a covalent link between the solid support and the oligomer.

The degree of oligomerisation is arbitrarily selected on these figures for the purpose of illustration and cannot be considered as a limitation.

One example of an electrode based on a material of the invention is depicted on FIG. 13A and is a favourite object of the invention.

Another example of an electrode based on a material of the invention is depicted on FIG. 13B and is a favourite object of the invention.

The assembly of the constituents of the electrode can be done using several pathways:

The conductive or semi-conductive material with a high specific surface can be first functionalized and then deposited on the conductive electrode material or, in a different order; deposition can be done first, followed by functionalization steps.

The material of the invention once deposited on a conductive support can be used as an electrode for electronic applications, like an electrode in fuel cells, especially hydrogen fuel cells or in an electrolyser, especially a water electrolyser. These new electrode materials show for the first time high rates of reduction of protons to hydrogen. Furthermore, the catalytic process occurs at low overpotentials. These materials combine the great surface area and conductivity of MWCNTs and the efficiency of molecular catalysts in reducing protons to hydrogen. Furthermore the favourite metal-organic complexes, nickel (II) diphosphine complexes of formula (II), are easy to synthesize, display great stability to air and are not poisoned by carbon monoxide.

The favourite surface modification technique is based on the reduction of functionalized aryldiazonium salts. This technique offers a versatile and controlled electrografting method for immobilization of redox catalysts onto electrodes. The high rate of heterogeneous electron transfer at the ITO/MWCNT or graphite/MWCNT electrode is maintained. Transparent electrodes based on CNTs can be obtained for applications in photoelectrochemical cells. (Trancik et al. Nano Letters 2008, 8, 982-987). This route towards modified electron is versatile and can be transposed to other high surface area carbon materials or metal oxide photoelectrodes. These low-cost and transparent electrodes can be readily integrated in energy conversion devices.

These air-stable nanostructured materials have proven their efficiency in the production of $H_2$ from $H^+$ and could at least compete with platinum in electrocatalytic devices. The material can be used either in organic medium or in water. These air-stable nanostructured materials have proven their efficiency in the catalytic oxidation of $H_2$.

The new catalytic materials of the invention show numerous advantages:

They use only a handful of metal atoms, by contrast to the particle approach. This can be done through the use of cheap, easy to synthesize ligands coordinating the metal atoms.

The catalytic activity of each metal atom is higher, so that the amount of metallic charge can be reduced.

Molecular catalysts are very selective towards their chemical substrate, as opposed to platinum nanoparticles that are irreversibly polluted by gas or organic pollutants.

The metals used are not necessarily noble metals.

The stability of the molecular catalyst is increased upon grafting by comparison with that reported in solution.

These new materials can be used as a cathodic active layer in a water electrolyser. As the metal-organic complex is known for being an active catalyst for hydrogen oxidation, these materials can also be used as anodic active layer in a hydrogen fuel-cell. More generally, this class of material could be used in any application requiring electrocatalysis provided the nature of the grafted catalyst has been adapted to the application (electroreduction of organic substrates such as ketone, oxygen formation from water, oxygen reduction for the cathodic active layer of a fuel cell, depollution of water using dechlorination of pollutants, $CO_2$ reduction . . . ).

BRIEF DESCRIPTION OF THE DRAWINGS

Figures

Scheme 2: Synthesis of $[Ni(P_2^{Ph}N_2^{R})_2](BF_4)_2$

Figure 2:
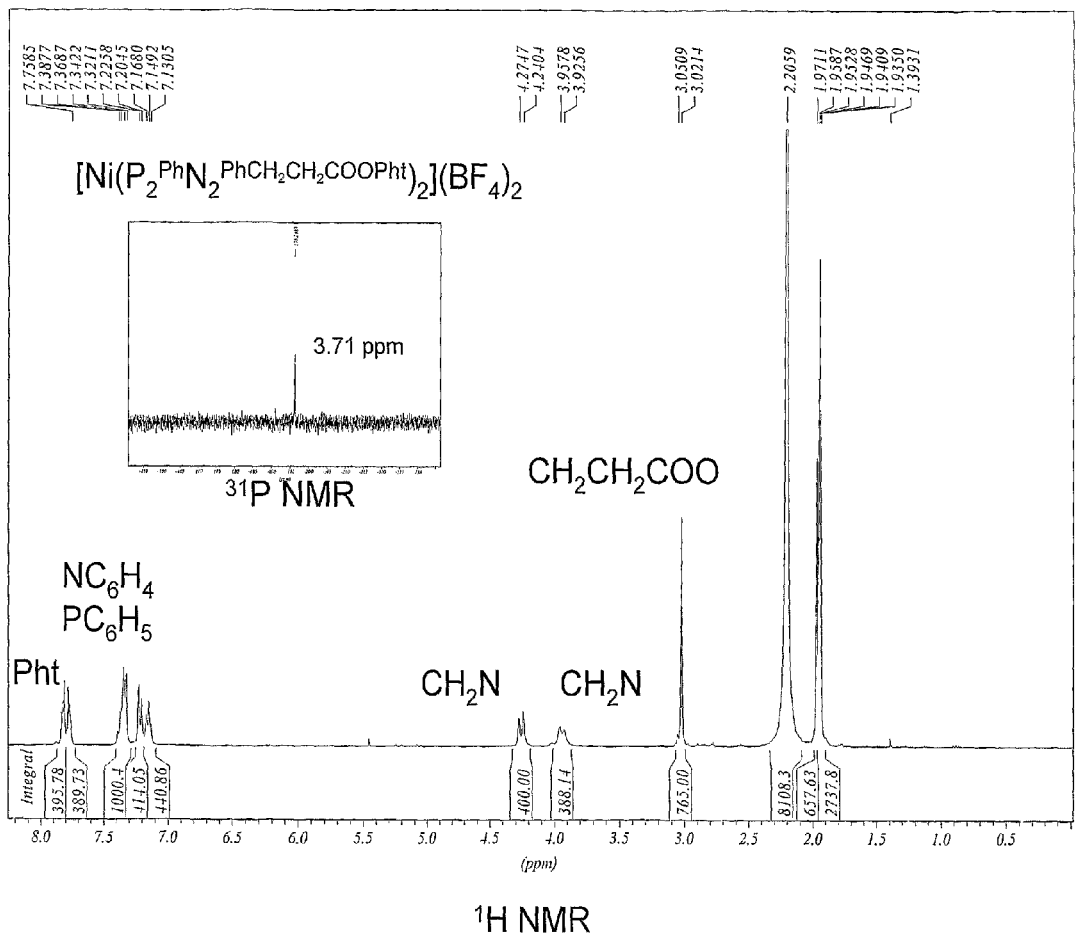

FIG. 2: $^1H$ and $^{31}P$ NMR spectrum of $[Ni(P_2^{Ph}N_2^{PhCH2CH2COOPht})_2](BF_4)_2$ in $CD_3CN$ FIG. 3: $^1H$ and $^{31}P$ NMR spectrum of $[Ni(P_2^{Ph}N_2^{CH2C16H9})_2](BF_4)_2$ in $CD_3CN$ FIG. 4: Cyclic voltammograms of $[Ni(P_2^{Ph}N_2^{R})_2](BF_4)_2$ (1 mmol.$L^{-1}$, glassy carbon working electrode, 50 mV.$s^{-1}$, MeCN—$Bu_4NPF_6$ 0.2 mol.$L^{-1}$, potentials are quoted versus the Ag/AgClO$_4$, 0.01 electrode): full line: R=PhCH$_2$CH$_2$COOPht, dashed line: R=CH$_2$C$_{16}$H$_9$R, dotted line: R=Ph.

FIG. 5a (left): Cyclic voltammograms of [Ni(P$_2^{Ph}$N$_2^{PhCH2CH2COOPht}$)$_2$](BF$_4$)$_2$ (1 mmol.L$^{-1}$) in CH$_3$CN in the presence of 0, 1.4, 2.7, 4.1, 7.5 and 11 equiv. of [DMFH]OTf (glassy carbon working electrode, 50 mV.s$^{-1}$, MeCN—Bu$_4$NPF$_6$ 0.2mol.L$^{-1}$, potentials are quoted versus the Ag/AgClO$_4$, 0.01 mol.L$^{-1}$ electrode)

FIG. 5b (right): Cyclic voltammetry of a solution of [Ni(P$_2^{Ph}$N$_2^{CH2C16H9}$)$_2$](BF$_4$)$_2$ (1 mmol.L$^{-1}$) in CH$_3$CN in the presence of 0, 1.4, 2.7, 4.1, 7.5 and 11 equiv. [DMFH]OTf (glassy carbon working electrode, 50 mV.s$^{-1}$, MeCN—Bu$_4$NPF$_6$ 0.2mol.L$^{-1}$, potentials are quoted versus the Ag/AgClO$_4$, 0.01 mol.L$^{-1}$ electrode)

FIG. 6: Trace of the ratio [I$_p^c$(H$^+$)/I$_p^c$(Ni)] (where I$_p^c$(H$^+$) is the peak current of the catalytic wave and I$_p^c$(Ni) is the peak current of a monoelectronic Ni-centered wave) towards the equivalents of [DMFH](OTf) for (▲) [Ni(P$_2^{Ph}$N$_2^{PhCH2CH2COOPht}$)$_2$](BF$_4$)$_2$ and (■) [Ni(P$_2^{Ph}$N$_2^{CH2C16H9}$)$_2$](BF$_4$)$_2$ FIG. 7: XPS spectrum of ITO/MWNT—PhCH$_2$CH$_2$—NH$_3^+$/—NH$_2$ electrode at N 1s binding energy level FIG. 8: Cyclic voltammetry (3 successive scans) at an functionnalized ITO/MWCNT—PhCH$_2$CH$_2$NH—[Ni(P$_2^{Ph}$N$_2^{PhCH2CH2CO}$)$_2$](BF$_4$)$_2$ electrode in MeCN—Bu$_4$NPF$_6$ 0.2 mol.L$^{-1}$ (50 mV.s$^{-1}$; potentials are quoted versus the Ag/AgClO$_4$, 0.01 mol.L$^{-1}$ electrode)

Figure 9:
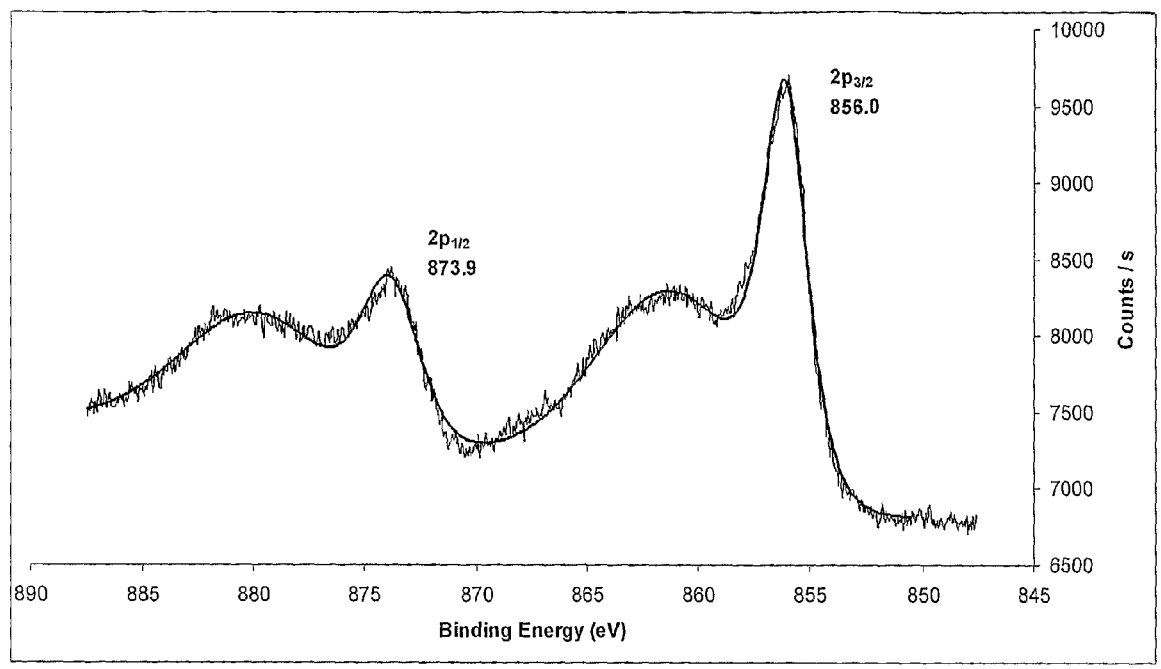

FIG. 9 XPS spectrum of a functionalized ITO/MWCNT—PhCH$_2$CH$_2$NH—[Ni(P$_2^{Ph}$N$_2^{PhCH2CH2CO}$)$_2$](BF$_4$)$_2$ electrode (Left: Ni 2p ; right: P 2p).

Figure 10:
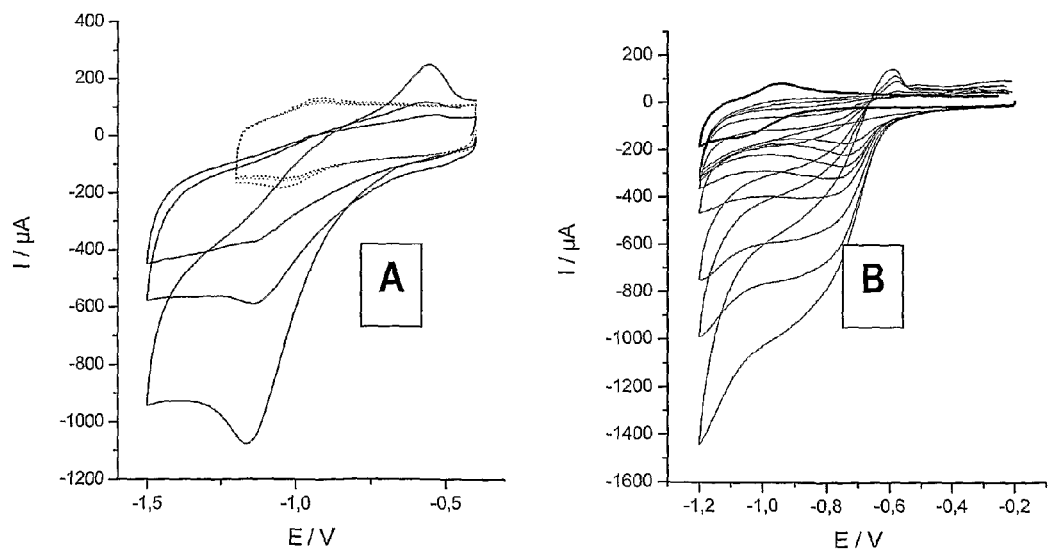

FIG. 10: Electrocatalytic behaviour of a (A) ITO/MWCNT electrode in the presence of various concentrations of [DMFH]OTf (0, 2, 3.5 and 7 mM) and (B) functionalized ITO/MWCNT—PhCH$_2$CH$_2$NH—[Ni(P$_2$N$_2^{PhCH2CH2CO}$)$_2$](BF$_4$)$_2$ electrode in the presence of various concentrations of [DMFH]OTf (0, 0.29, 0.60, 0.90, 1.17, 1.75, 2.34, 3.51, 5.85, 11.7 mM) in MeCN—Bu$_4$NPF$_6$ 0.2M (50 mV.s$^{-1}$; potentials are quoted versus the Ag/AgClO$_4$, 0.01 mol.L$^{-1}$ electrode)

Figure 11:
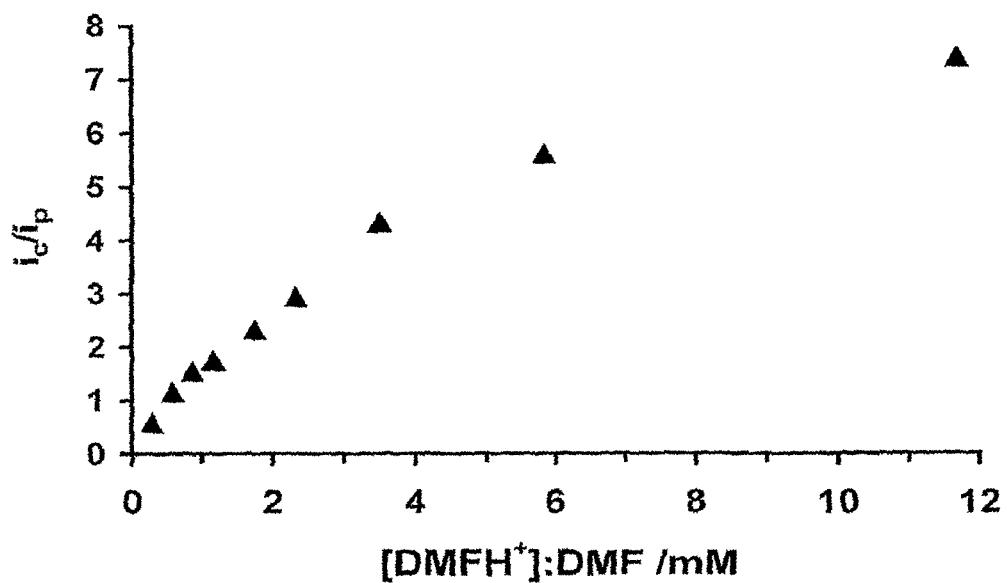

FIG. 11: Trace of the ratio [I$_p^c$(DMFH$^+$)/I$_p^c$(Ni)] towards the concentration of [DMFH](OTf) for a functionalized ITO/MWCNT—PhCH$_2$CH$_2$NH—[Ni(P$_2^{Ph}$N$_2^{PhCH2CH2CO}$)$_2$](BF$_4$)$_2$ electrode.

Figure 12:
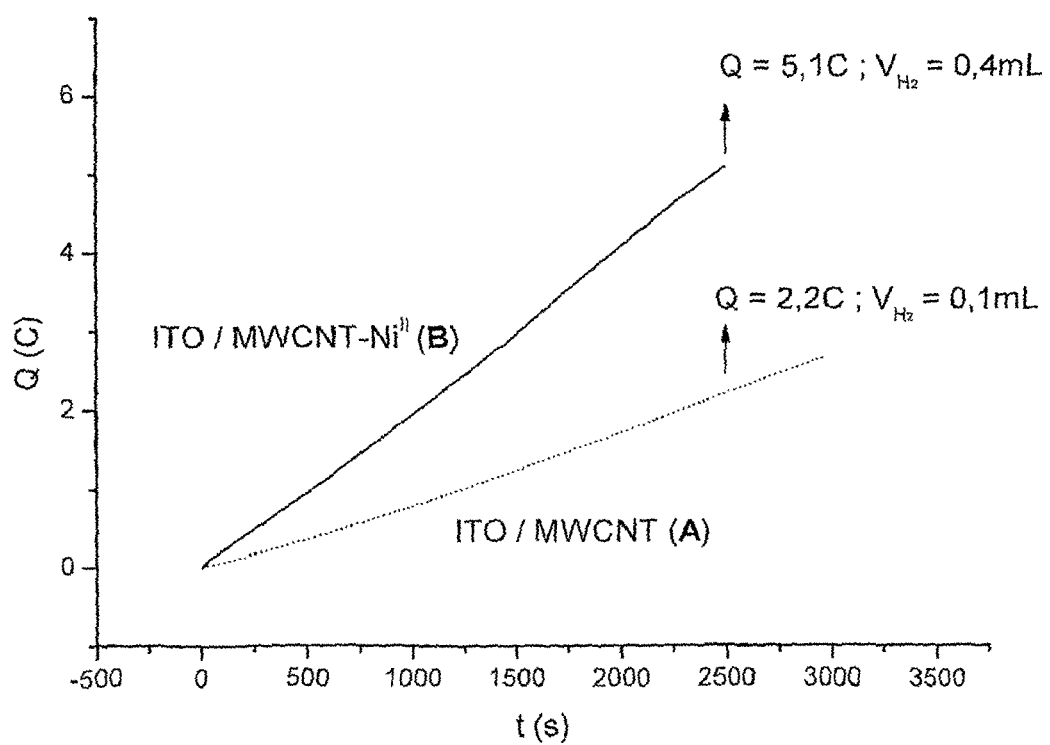

FIG. 12: Coulometry at (A) an ITO/MWCNT electrode and (B) an ITO/MWNT—PhCH$_2$CH$_2$NH—[Ni(P$_2^{Ph}$N$_2^{PhCH2CH2CO}$)$_2$](BF$_4$)$_2$ (area: 1 cm$^{-1}$) poised at –0.5 V vs Ag/AgCl in CH$_3$CN solution of [DMFH](OTf) (0.06 mol.L$^{-1}$) and n-Bu$_4$NBF$_4$ (0.1 mol.L$^{-1}$). The volume of the evolved hydrogen as a function of the charge is represented in the inset.

Figure 13:
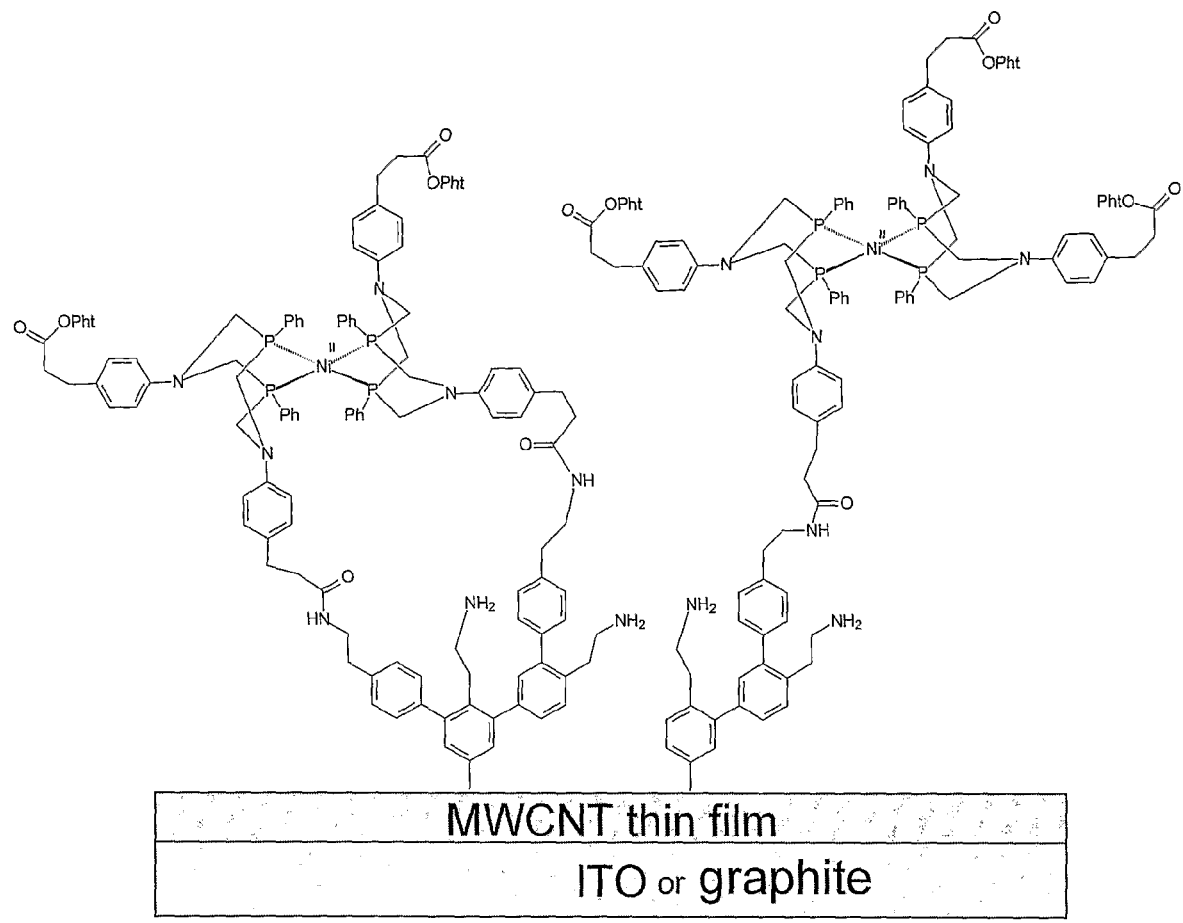
Figure 13:
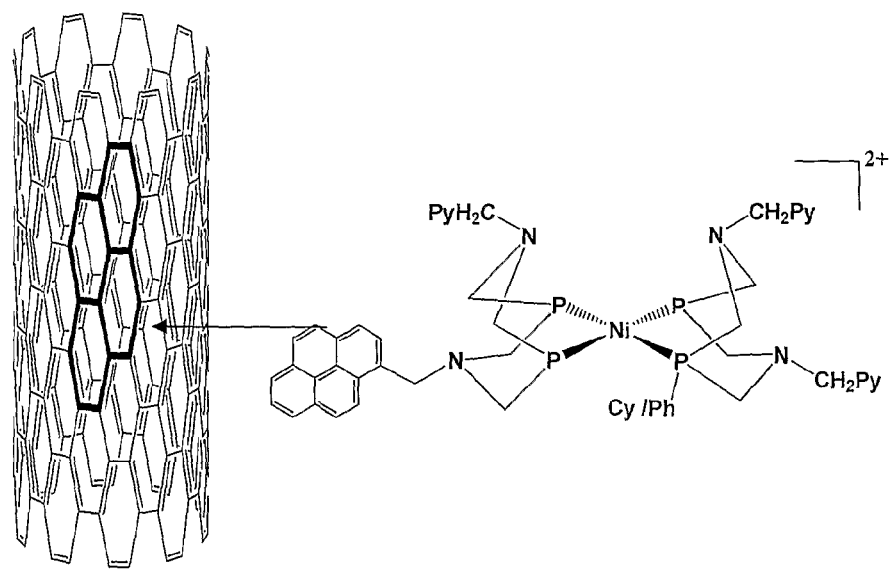

FIG. 13A: Representation of the structure of an ITO/MWNT—PhCH$_2$CH$_2$NH—[Ni(P$_2^{Ph}$N$_2^{PhCH2CH2CO}$)$_2$](BF$_4$)$_2$ electrode.

Figure 14:
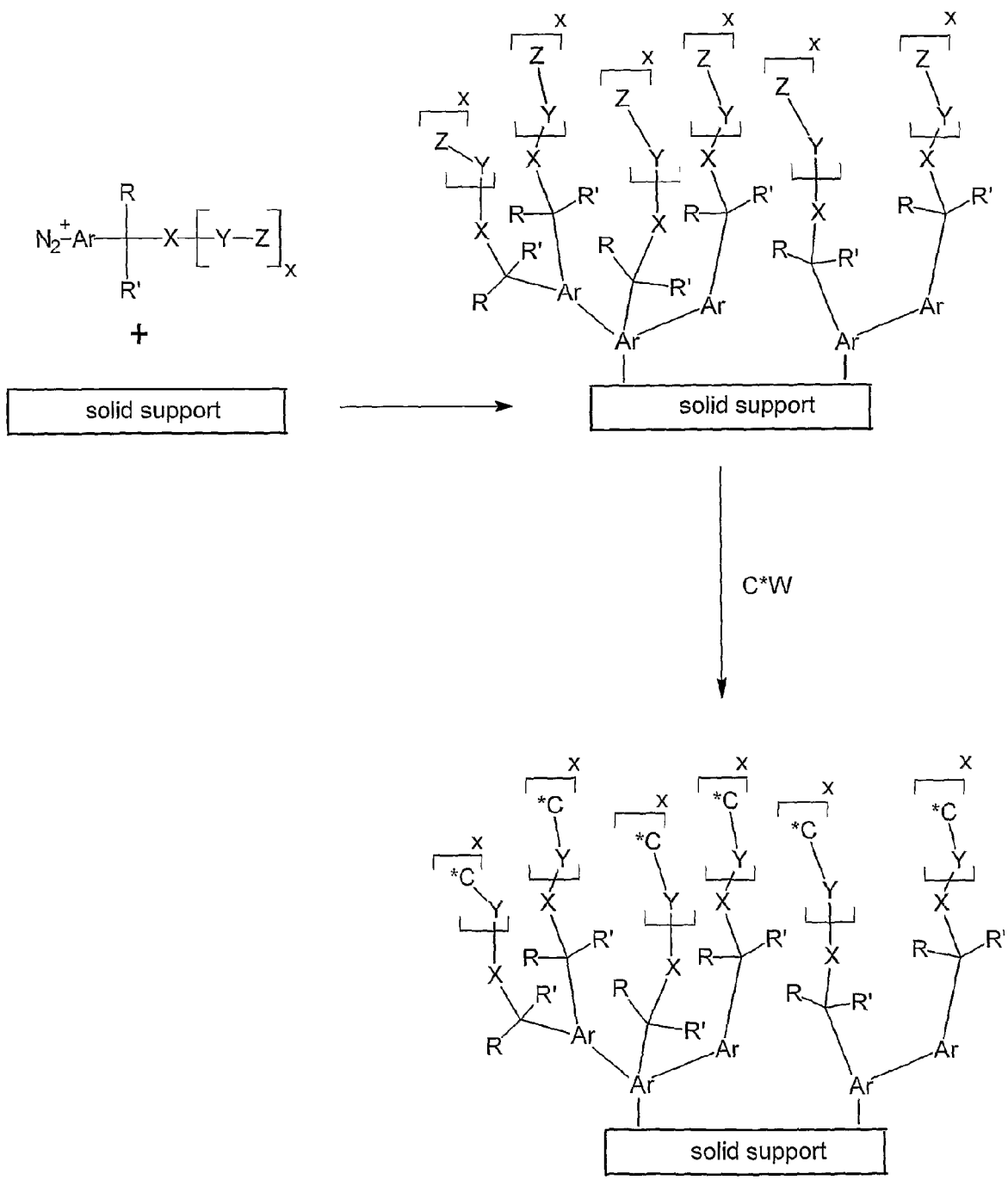
Figure 15:
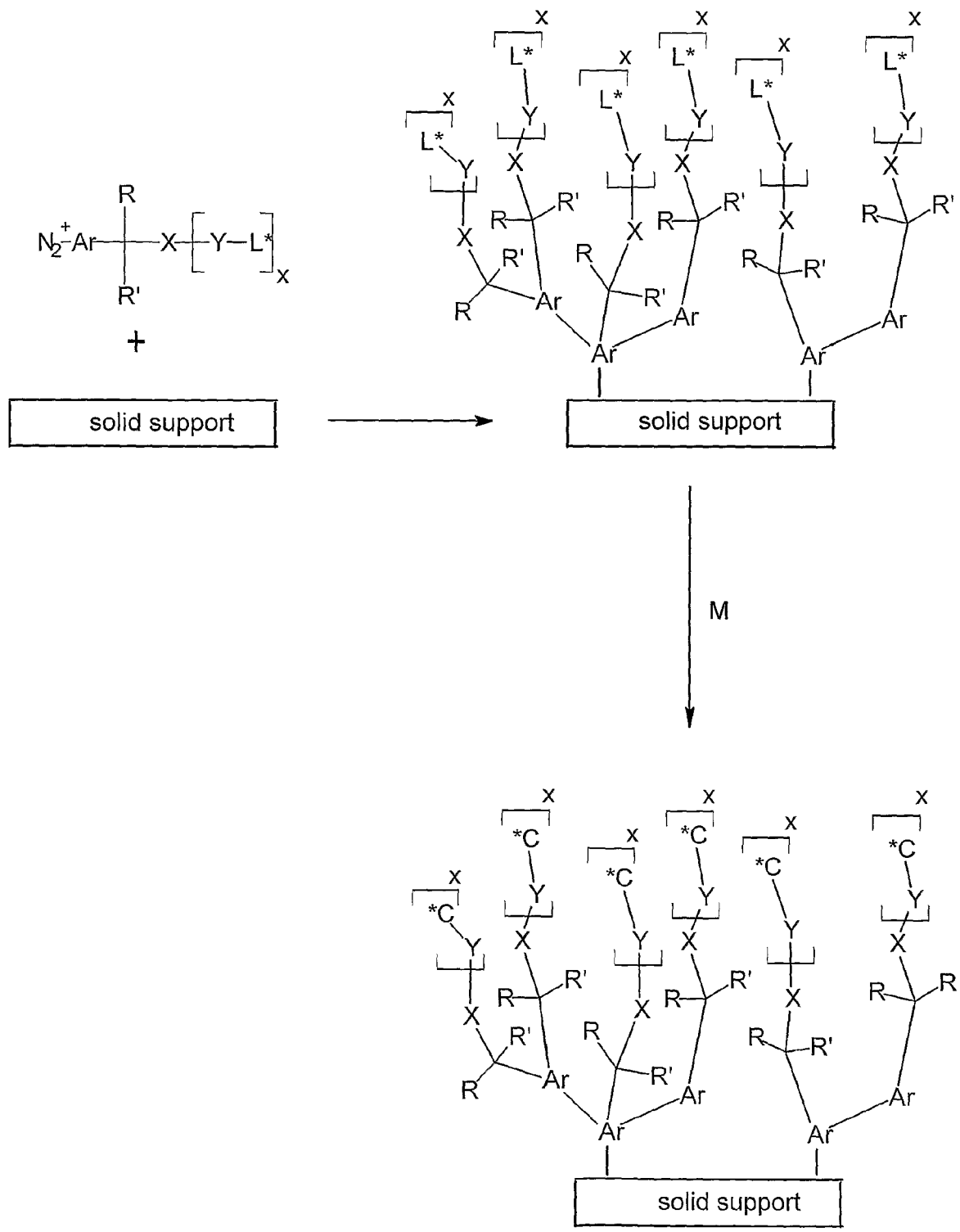
Figure 16:
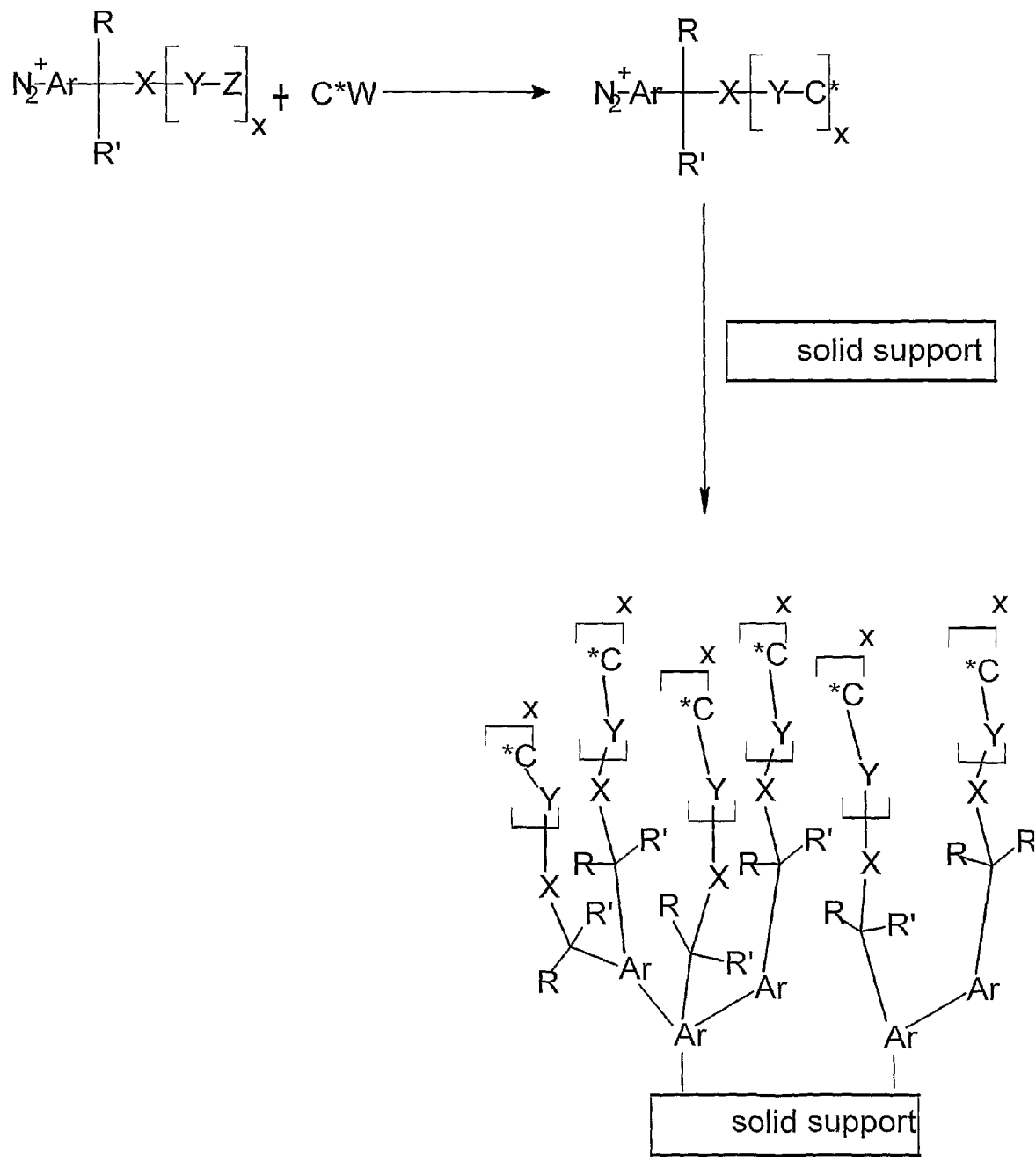

FIG. 13B: Representation of the structure of a PTFE/MWCNT—PhCH$_2$CH$_2$NH—[Ni(P$_2^{Ph}$N$_2^{PhCH2CH2CO}$)$_2$](BF$_4$)$_2$ electrode FIGS. 14 to 16 schematically illustrate the steps from the preparation of materials of the invention.

Figure 17A:
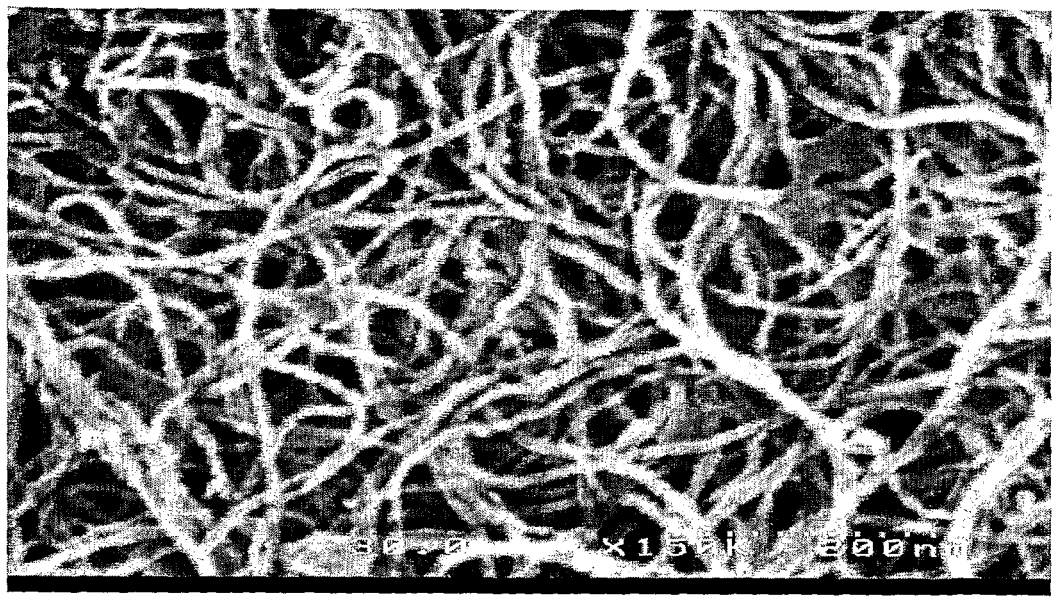
Figure 17B:
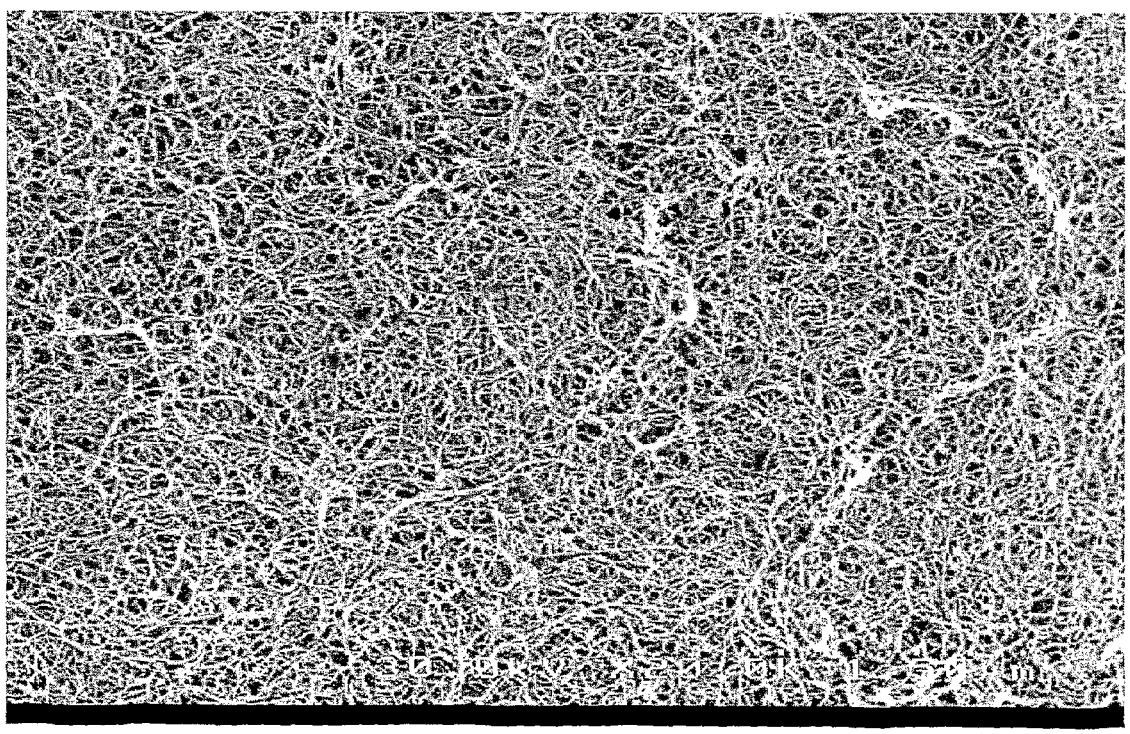

FIGS. 17A and 17B: MEB image of a a functionalized ITO/MWCNT—PhCH$_2$CH$_2$NH—[Ni(P$_2^{Ph}$N$_2^{PhCH2CH2CO}$)$_2$](BF$_4$)$_2$ electrode FIGS. 18A and 18B: Devices for electrochemical measurement on membrane electrode assemblies containing gas diffusion layers. (1) Membrane Electrode Assembly (MEA), (1.0) Gas diffusion electrode (14 mm disc diameter), (1.1) catalytic material, (1.2) Nafion® NRE 212 CS membrane, (3) gold grid, (4) PTFE gasket, (5) platinum mesh, (6) mercury sulfate electrode reference, (7) nitrogen bubbling and (8) gas flow nitrogen or hydrogen.

Figure 19:
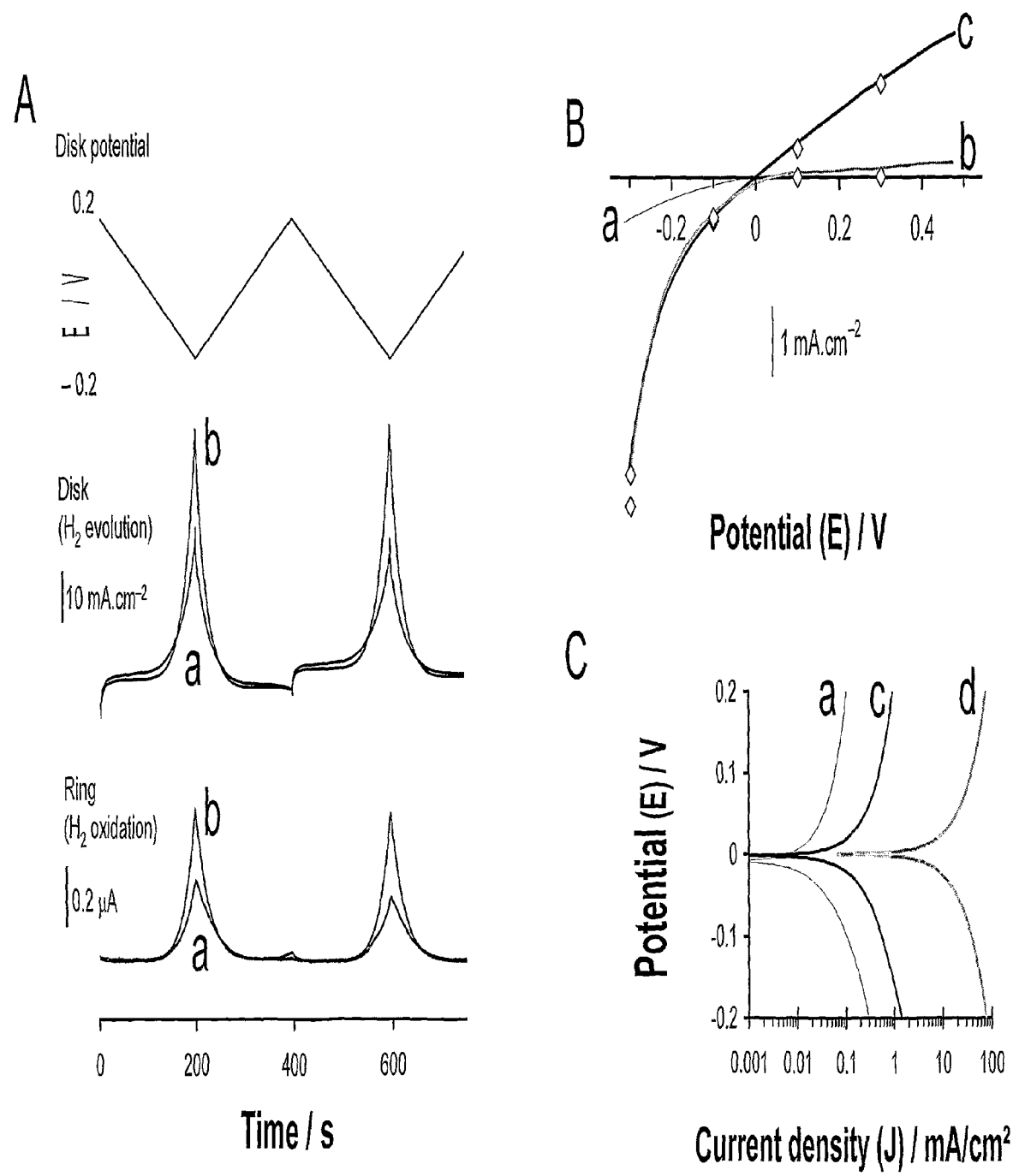

FIG. 19: Electrochemical measurements for hydrogen evolution and uptake from 0.5 M H$_2$SO$_4$ aqueous solution recorded at MEA consisting of a gas diffusion layer (GDL) assembled with a Nafion membrane. The GDL is modified by MWCNTS or MWCNTs functionalized with a nickel catalyst using linker (IC). A: rotating disk measurements. B. linear voltammetry measurements (2 mV.s$^{-1}$). C: Logarithmic representation of linear voltametry measurements with additional comparison with a platinum-coated GDL.

Figure 20:
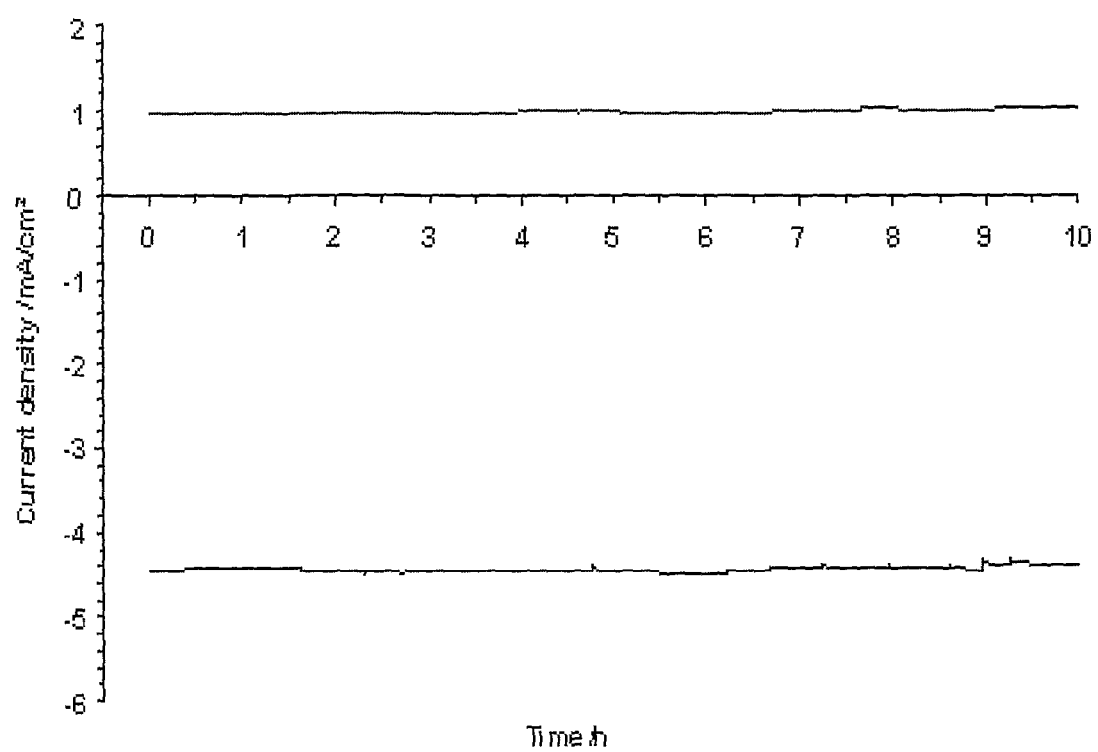

FIG. 20: Long-run electrolysis experiments for both hydrogen evolution (Electrolysis at –0.3 V vs NHE) and oxidation (Electrolysis at +0.3 V vs NHE) carried out on a membrane electrode assembly functionalized with the nickel catalyst via the diazonium route.

Figure 21:
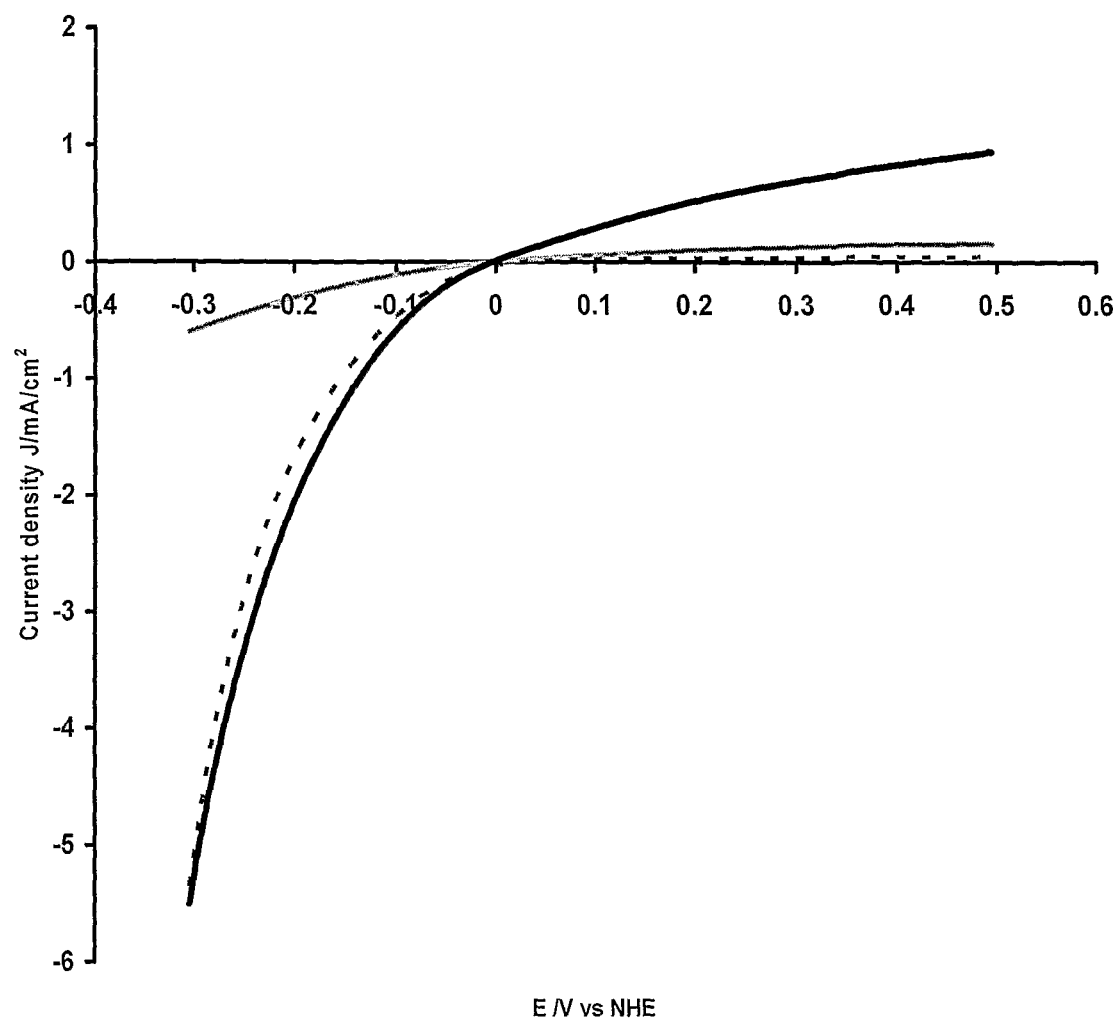

FIG. 21: Evolution of current density as a function of the potential for both hydrogen evolution and oxidation from 0.5 M H$_2$SO$_4$ aqueous solution recorded at a MEA consisting of a gas diffusion layer (GDL) functionalized with a nickel catalyst using linker (IA) assembled with a Nafion membrane (2 mV.s$^{-1}$).

DETAILED DESCRIPTION OF THE INVENTION

Experimental Part

Materials. All reactions were routinely performed under an inert atmosphere of argon in a glove box or using standard Schlenk techniques. Solvents were degassed and distilled under argon. Diethyl ether was distilled by refluxing over Na/benzophenone; ethanol was distilled by refluxing over magnesium diethoxide; dry acetonitrile and dichloromethane were obtained by distillation on CaH$_2$. NMR solvents (Eurisotop) were deoxygenated by three freeze-pump-thaw cycles and stored over molecular sieves. Commercial dimethylformamide for electrochemistry was degassed by bubbling nitrogen through it. The supporting electrolyte (n-Bu$_4$N)BF$_4$ was prepared from (n-Bu$_4$N)HSO$_4$ (Aldrich) and NaBF$_4$ (Aldrich) and dried overnight at 80° C. under vacuum. [Ni(MeCN)$_6$](BF$_4$)$_2$ was prepared according to previously described procedures [B. J. Hathaway, A. E. Underhill, J. Chem. Soc. 1960, 3705; B. J. Hathaway, D. G. Holah, A. E. Underhill, J. Chem. Soc. 1962, 2444]. Other chemicals were used as received. Commercial 3100 grade Multi-walled Carbon Nanotubes (>95%) were obtained from Nanocyl. Commercial grade C100 Multi-walled Carbon Nanotubes (>95%) were obtained from Arkema Carbon nanotubes were used as received, without any purification step. The ITO substrates were provided by Präzision Glas & Optik, GmbH (PGO).

Methods and Instrumentation:

NMR spectra were recorded at room temperature in 5 mm tubes on a Bruker AC 300 spectrometer equipped with a QNP probehead, operating at 300.0 MHz for $^1$H, 75.5 MHz for $^{13}$C and 121.5 MHz for $^{31}$P or a Bruker AVANCE DRX 400 operating at 400.0 MHz for $^1$H. Solvent peaks are used as internal references relative to Me$_4$Si for $^1$H and $^{13}$C chemical shifts; $^{31}$P NMR spectra were proton-decoupled and referenced to H$_3$PO$_4$ (85%). ESI mass spectra were recorded with a Finnigan LCQ thermoquest ion-trap. Elemental analyses were done at the Microanalyses Laboratory at ICSN/CNRS, Gif/Yvette, France.

For Infrared spectroscopy (IR) a Bruker Vertex 70 spectrometer (resolution 2 cm$^{-1}$, spectra were collected with 256 scans, MCT detector), equipped with a Pike Miracle plate for ATR. UV-Vis spectra were recorded with a Perkin Elmer Lambda 650 spectrometer. X-ray photoelectron spectra (XPS) were recorded on a Kratos Analytical Axis Ultra DLD, using an Al Kα source monochromatized at 1486.6 eV. We used a hemispheric analyzer working at pass energy of SO eV for the global spectrum, and 20 eV when focusing on the sole core levels. The morphology of the obtained MWCNT electrodes was investigated by SEM Hitachi S-4500.

Electrochemical Measurements:

Electrochemical analysis was done using an EG&G potentiostat, model 273A. The electrochemical experiments were carried out in a three-electrode electrochemical cell under a highly controlled argon dry atmosphere in a glove box. The working electrodes were those described below. The auxiliary electrode was a platinum or graphite foil. The reference electrode was based on the $Ag/AgClO_4$ $10^{-2}$ M couple. Alternatively, a silver/silver chloride electrode has been used. These reference electrodes have been calibrated after each experiment by adding ferrocene in the solution and measuring its half-wave potential. Unless otherwise stated, all potentials given in this work are with respect to the ($Ag/AgClO_4$) reference electrode. The experiments were conducted in anhydrous dichloromethane or acetonitrile (water content <50 ppm) with tetrabutylammonium hexafluorophosphate $[Bu_4N]PF_6$ as the supporting electrolyte. Additions of [DMFH](OTf) were made by syringe as a 2/1 (mol:mol) fresh mixture of dimethylformamide (4.9 mL) and triflic acid (2.8 mL) with a density of 1.28 and a $[DMFH]^+$ concentration of 4.1 M.

For bulk electrolysis experiments in non-aqueous media, a tight cell was used, connected to a U tube allowing volumetric monitoring of the evolved gas at atmospheric pressure. The platinum-grid counter electrode was placed in a separate compartment connected by a glass-frit and filled with the electrolytic solution. Hydrogen accumulated in the cell was tested for purity using a Delsi Nermag DN200 GC chromatograph equipped with a 3 m Porapack column and a thermal conductivity detector (TCD). Nitrogen under 1 bar was used as the carrier gas. The whole apparatus was thermostated at 45° C. Under these conditions, pure hydrogen has an elution time of 78 s.

Steady State Rotating Disk-Ring Electrode measurements were carried out using a Pine E7R9 series GCPT electrode connected to a Bio-logic VMP2 multipotentiostat. A $Hg/Hg_2SO_4$ electrode (E=0.68 V vs NHE) was used as reference and a platinum wire was used as auxiliary electrode. The material was formulated as an ink, mixing the catalyst powder with the same amount of isopropanol and 5 wt % Nafion D-521 dispersion manufactured by DuPont Fluoroproducts (http://www2.dupont.com/Fuel_Cells/en_US/assets/downloads/dfc103.pdf) in order to reach 5 wt % of Nafion in solid contents after drying. After homogenization in ultrasonic bath for 15 minutes, a drop corresponding to 50 µg of powder was deposited on the 0.196cm² vitreous carbon disk electrode and dried at room temperature. Hydrogen evolved at the disk electrode was monitored at the concentric platinum ring electrode poised at 600 mV vs NHE. Calibration was used using a sample of commercial platinum-loaded carbon material (BASF Pt/C 20 wt %).

Characterisation of functionalized gas diffusion layers was achieved with a half-cell holder for gas diffusion electrodes set-up (see FIGS. 18A and 18B). Gas diffusion electrodes (1.0) (14 mm disc diameter) on which the catalytic material (1.1) has been deposited and Nafion® NRE 212 CS membrane (1.2) (DuPont) were directly bonded together by hot-pressing process (4 MPa at 135° C. for 2 minutes and 30 seconds). The obtained Membrane Electrode Assembly (MEA) (1) was inserted in the sample holder with the gas diffusion layer face up. The middle of the Nafion membrane (ø8 mm) was then exposed to the liquid electrolyte (0.5M $H_2SO_4$) while the same surface area of the gas diffusion layer is fed with a nitrogen or hydrogen flow (8) set at 20 mL.min⁻¹.

A gold grid (3) provides the electrical contacts and a PTFE gasket (4) set on the membrane side ensure the tightness of the device.

A three-electrode, two-compartment set-up containing 40 ml of solution deaerated by continuous nitrogen bubbling (7) was used. A platinum mesh (5) acted as counter electrode and the reference was a mercury sulfate electrode (6) (Radiometer MSE $Hg/Hg_2SO_4$–$E_0$=0.68V vs NHE). Electrochemical experiments were performed on a computer controlled Bio-logic VMP2 potentiostat. Polarization curves were conducted following the same test plan: while a gas flow (8) (nitrogen or hydrogen) is set at 20 ml.min⁻¹, 5 voltammetry cycles (CV) from $0.5V_{NHE}$ to $-0.3V_{NHE}$ at 2 mV.s⁻¹ were recorded.

Ohmic resistance of the MEAs were measured by Electrochemical Impedance Spectroscopy after five minutes stabilization at various potentials (−0.3, −0.1, 0.1 and 0,3 V vs NHE). The amplitude of the applied signal was 10 mV and 10 measurements per decade were performed between 200 kHz and 100 mHz. Ohmic resistance was estimated by modelling the experimental results with an equivalent electronic circuit $R_\Omega$ ($R_{CT}$//$HQ_{DL}$) consisting of a resistance in series with a constant phase element and another resistance set in parallel. $R_\Omega$ corresponds to the ohmic resistance of the full device, $Q_{DL}$ is a constant phase element relative to capacitive effects (double layer capacitance and pseudo-capacitance) and $R_{CT}$ is attributed to the charge transfer resistance. A typical ohmic resistance found for our MEA is 3-5 Ω. Owing to the low current values, no correction for ohmic drop needs to be performed.

During controlled-potential coulometry experiments, the gas flowing over the GDL was sampled (100 µL) every 2 minutes and analysed using a Perkin-Elmer Clams 500 gas chromatograph equipped with a porapack Q 80/100 column (6'⅛") thermostated at 40° C. and a TCD detector thermostated at 100° C. Calibration was used using a commercial GDL loaded with platinum active layer (BASF LT140EWSI, platinum loading 0.5 mg.cm⁻²).

Synthesis

All reagents and chemicals were purchased from Aldrich. Reagents and chemicals were used as received except when mentioned. $[Ni(MeCN)_6](BF_4)_2$ was prepared according to known procedures [B. J. Hathaway, A. E. Underhill, *J. Chem. Soc.* 1960, 3705; B. J. Hathaway, D. G. Holah, A. E. Underhill, J. Chem. Soc. 1962, 2444].

4-(2-ammonioethyl)benzenediazonium tetrafluoroborate

A 50% solution of tetrafluoroboric acid in $Et_2O$ (0.5mL, 3.7 mmol) was added to a solution of 4-(2-aminoethyl)aniline (0.5mg, 3.7 mmol) in MeCN (Amp at −40° C. under argon. The mixture was stirred 10 min, then nitrosyl tetrafluoroborate (450 mg, 3.8 mmol) was added dropwise. After 30 min of stirring at −40 ° C. $Et_2O$ (100 mL) was added. The white precipitate obtained was filtered and washed twice with $Et_2O$ to give a white powder (1.18 g, 99%).

¹H ($CD_3CN$): 3.26 (m, 2H, $CH_2CH_2NH_3^+$), 3.31 (m, 2H, $CH_2CH_2NH_3^+$), 7.82 (d, 2H, J =9Hz, $C_6H_4$), 8.44 (d, 2H, J = 9Hz, $C_6H_4$)

IR: ν(cm⁻¹)=3270, 3201, 3113, 2285, 1589, 1508, 1019, 928, 851, 820, 781

Figure 1:
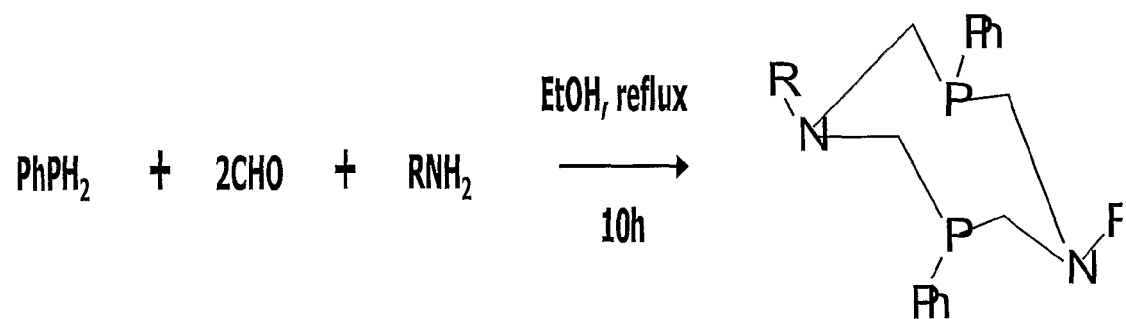
FIG. 1 illustrates the synthesis methods for a metal organic complex as disclosed in the examples Scheme 1: Synthesis of $P_2^{Ph}N_2^{R}$ (in the examples hereunder R=$CH_2C_{16}H_9$ or R=$PhCH_2CH_2COOPht$)
Figure 1:
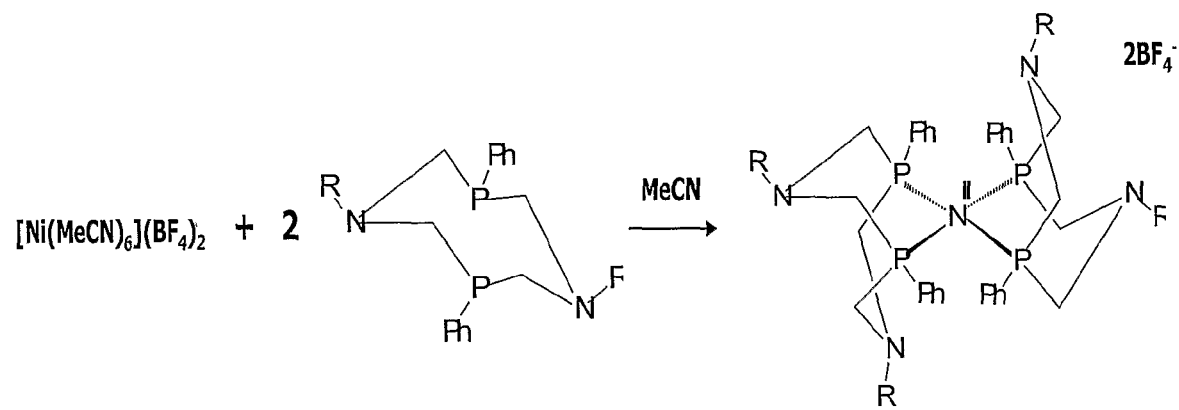

$P_2^{Ph}N_2^{PhCH2CH2COOH}$ (Scheme 1/FIG. 1)

A solution of phenylphosphine 10% in hexane (3.3 mL, 3.0 mmol) was added dropwise to a solution of paraformaldehyde (180 mg, 6.0 mmol, 2 equiv.) in degassed EtOH (40 mL). The mixture was heated under stirring at 80° C. for 40 min. 3-(4-aminophenyl)propanoic acid (496 mg, 3.0 mmol, 1 equiv.) was added and the solution refluxed overnight. The solution was allowed to cool down to RT. A white precipitate (1.43 g, 2.4 mmol, 80%) was filtrated and washed with EtOH.

$^{31}$P (DMSO-d$_6$): −52.0 (br, s)

$^1$H (DMSO-d$_6$): 2.42 (t, 2H, CH$_2$CH$_2$COO, J=7Hz), 2.67 (t, 2H, CH$_2$CH$_2$COO, J=7Hz), 4.12 (m, 4H, NCH$_2$P), 4.54 (m, 4H, NCH$_2$P), 6.57-7.03 (m, 8H, NC$_6$H$_4$), 7.47-7.69 (m, 10H, PC$_6$H$_5$), 12.00 (s, 1H, COOH)

IR: ν(cm$^{-1}$)=2961, 2921, 1708, 1613, 1515, 1456, 1435, 1379, 1243, 1190, 799, 788, 746

P$_2^{Ph}$N$_2^{PhCH2CH2COOPht}$ (Scheme 1/FIG. 1)

A solution of P$_2^{Ph}$N$_2^{PhCH2CH2COOPht}$ (320 mg, 0.53 mmol), 1-ethyl-3-(3-dimethylaminopropyl)-carbodiimide (EDC, 191 mg, 1.23 mmol, 2.3 equiv.) and N-hydroxyphtalimide (200 mg, 1.23 mmol, 2.3 equiv.) in DMF (2 mL) was stirred during 4 h. Water (80 mL) was added yielding a white precipitate which was filtrated and washed with acetone to give a white powder (310 mg, 0.35 mmol, 65%).

$^{31}$P (CD$_3$CN): −52.6 (br s)

$^1$H (CD$_3$CN): 2.83 (t, 2H, CH$_2$CH$_2$COO, J=7 Hz), 2.95 (t, 2H, CH$_2$CH$_2$COO, J=7 Hz), 4.12 (m, 4H, NCH$_2$P), 4.53 (m, 4H, NCH$_2$P), 6.59-7.11 (m, 8H, NC$_6$H$_4$), 7.46-7.67 (m, 10H, PC$_6$H$_5$), 7.90-7.97 (8H, H Pht)

[Ni(P$_2^{Ph}$N$_2^{PhCH2CH2COOPht}$)$_2$](BF$_4$)$_2$ (Scheme 2/FIG. 1)

A solution of [Ni(MeCN)$_6$](BF$_4$)$_2$ (50 mg, 0.104 mmol) was stirred at RT during 3h in the presence of P$_2^{Ph}$N$_2^{PhCH2CH2COOPht}$ (200 mg, 0.225 mmol, 2.2 equiv.) in MeCN (10 mL). The solution was concentrated under vaccum and Et$_2$O was added to precipitate a red powder. After filtration, the red product (90 mg, 0.045 mmol, 40%) was washed twice with Et$_2$O and dried in vacuum.

$^{31}$P (CD$_3$CN): 3.71 (br s)

$^1$H (CD$_3$CN): 3.02 (m, 16H, CH$_2$CH$_2$COO), 3.93 (d, 8H, J=5.6 Hz, NCH$_2$P), 4.25 (d, 8H, J=5.6 Hz, NCH$_2$P), 7.13-7.23 (m, 16H, NC$_6$H$_4$), 7.32-7.39 (m, 20H, PC$_6$H$_5$), 7.7-7.9 (16H, H Pht)

IR: ν(cm$^{-1}$)=1743, 1508, 1187, 1057, 879, 697

UV/Vis (CH$_3$CN): λ=290 nm (ε=24000), 480 nm (ε=1500)

P$_2^{Ph}$N$_2^{CH2C16H9}$

Pyrenemethylamine hydrochloride (535 mg, 2.0 mmol) was added to a solution of NaOH (120 mg, 3.0 mmol) in water (40 mL). The resulting suspension was extracted with CH$_2$Cl$_2$ (3×20 mL). Removal of the solvent under vaccum.yields a white power of pyrenemethylamine (415 mg, 1.80 mmol).

A solution of phenylphosphine 10% in hexane (1.9 mL, 1.72 mmol) was added dropwise to a solution of paraformaldehyde (100 mg, 3.33 mmol 2 equiv.) in EtOH (40 mL). The mixture was heated under stirring at 80° C. for 40 min. Pyrenemethylamine (400 mg, 1.72 mmol, 1 equiv.) was added and the solution was refluxed overnight. Upon cooling to RT, a white precipitate (1.07 g, 1.46 mmol, 85%) formed which was filtrated and washed with EtOH.

$^{31}$P (CD$_3$CN): −48.0 (br s)

IR: ν(cm$^{-1}$)=3044, 2872, 2830, 1250, 1068, 837, 739, 711

[Ni(P$_2^{Ph}$N$_2^{CH2C16H9}$)$_2$](BF$_4$)$_2$

A solution of [Ni(MeCN)$_6$](BF$_4$)$_2$ (70 mg, 0.14 mmol) was stirred at RT during 3h in the presence of P$_2^{Ph}$N$_2^{PhCH2CH2COOPht}$ (200 mg, 0.2 mmol, 2 equiv.) in MeCN (10 mL). The solution was filtrated and concentrated under vaccum. Et$_2$O was added to precipitate an orange powder. After filtration, the red-orange product (220 mg, 0.13 mmol, 90%) was washed twice with Et$_2$O and dried in vacuum.

$^{31}$P (CD$_3$CN): 3.37 (br s)

$^1$H (CD$_3$CN): 3.14 (br d, 8H, J=20 Hz, NCH$_2$P), 3.42 (d, 8H, J=12 Hz, NCH$_2$C$_{16}$H$_9$), 4.50 (br d, 8H, J=55 Hz, NCH$_2$P), 6.48-6.92 (m, 20H, PC$_6$H$_5$), 7.73-8.04 (36H, C$_{16}$H$_9$)

IR; ν(cm$^{-1}$)=3061, 1592, 1494, 1194, 1050, 746, 690

UV/Vis (CH$_3$CN): λ=313 nm (ε=51000), 328 nm (ε=105000), 344 nm (ε=130000), 471 nm (ε=1400)

Preparation of MWCNT Electrodes

ITO/MWCNT

ITO/MWCNT electrodes were made by filtration technique on mixed cellulose ester membrane of a suspension of MWCNT (0.1 mg) in water (80 mL) [2]. The membrane was deposited on an ITO wafer and dissolved through washings with MeCN and acetone. Samples were further heated at 100° C.

Graphite/MWCNT

Graphite/MWCNT electrodes were made by filtration technique on mixed cellulose ester membrane of a suspension of MWCNT (0.1 mg) in water (80 mL) (Wu et al., Science 305, 2004, 1273-1276). The membrane was deposited on a graphite wafer and dissolved through washings with MeCN and acetone. Samples were further heated at 100° C.

PTFE/MWCNT

PTFE/MWCNT electrodes were made by filtration of a suspension of MWCNT in EtOH on a PTFE membrane yielding a so-called PTFE/MWCNT bucky paper.

GDL/MWCNTs

MWCNTs (10 mg) were dispersed in pure water (250 mL) and sonicated during 30 min. The solution was carefully decanted overnight. The supernatant (100 mL) with a mass concentration of 0.295 mg/L (determinated via UV-visible absorption) was then filtered on a GDL disc (BASF LT1200W, 3 cm$^2$) resulting in the deposition of ~0.03 mg of MWCNTs. Samples were further heated at 100° C. for 1h.

Functionalization of MWCNT Electrodes Using Linker (IC)

ITO/MWCNT and GDL/MWCNT

The ITO/MWCNT and GDL/MWCNT electrodes were used as working electrodes in a three-electrode cell in the presence of 4-(2-ammonioethyl)benzenediazonium tetrafluoroborate (1 mmol.L$^{-1}$). Electrografting was performed though reduction of the diazonium salt. This can be done either using controlled potential coulometry at E$_p$=−0.26V or cyclic voltammetry (recording 3 cycles at 20 mV.s$^{-1}$ between 0.4V and −0.4V).

The Ni complex was introduced by a post-functionalization step based on the formation of an amide linkage between the amine residue introduced at the surface of the MWCNT electrode and the activated ester group of [Ni(P$_2^{Ph}$N$_2^{PhCH2CH2COOPht}$)$_2$](BF$_4$)$_2$. This step was achieved by dipping the wafer in a solution of [Ni(P$_2^{Ph}$N$_2^{PhCH2CH2COOPht}$)$_2$](BF$_4$)$_2$ (0.5 mmol.L$^{-1}$) in CH$_3$CN in the presence of Et$_3$N (2 mmol.L$^{-1}$). The solution was stirred overnight. XPS and electrochemistry experiments confirmed the covalent grafting of Ni complexes to MWCNTs. The structure of the grafted electrode can be represented by the scheme illustrated on FIG. 13A.

Functionalization of MWCNT Electrodes Using Linker (IC)

PTFE/MWCNT

Functionalized PTFE/MWCNT bucky papers were directly prepared by filtration of a suspension of MWCNTs (0.1 mg) in a EtOH/CH$_2$Cl$_2$ mixture (80/2 v:v, 80 mL) in the presence of [Ni(P$_2^{Ph}$N$_2^{CH2C16H9}$)$_2$](BF$_4$)$_2$ (5 mg). Π-stacking of the Ni complex bearing pyrene groups was conformed by XPS analysis and electrochemistry. The complex is illustrated on FIG. 13B.

GDL/MWCNT

A solution of [Ni(P$_2^{Ph}$N$_2^{CH2C16H9}$)$_2$](BF$_4$)$_2$ (5 mg) in CH$_2$Cl$_2$ mixture (10 mL) was slowly filtered onto GDL/

MWCNT electrodes. Π-stacking of the Ni complex bearing pyrene groups was confirmed by XPS analysis and electrochemistry.

Results

Functionalization of GDL/MWCNT Electrodes Using Linker (IC)

Figure 3:
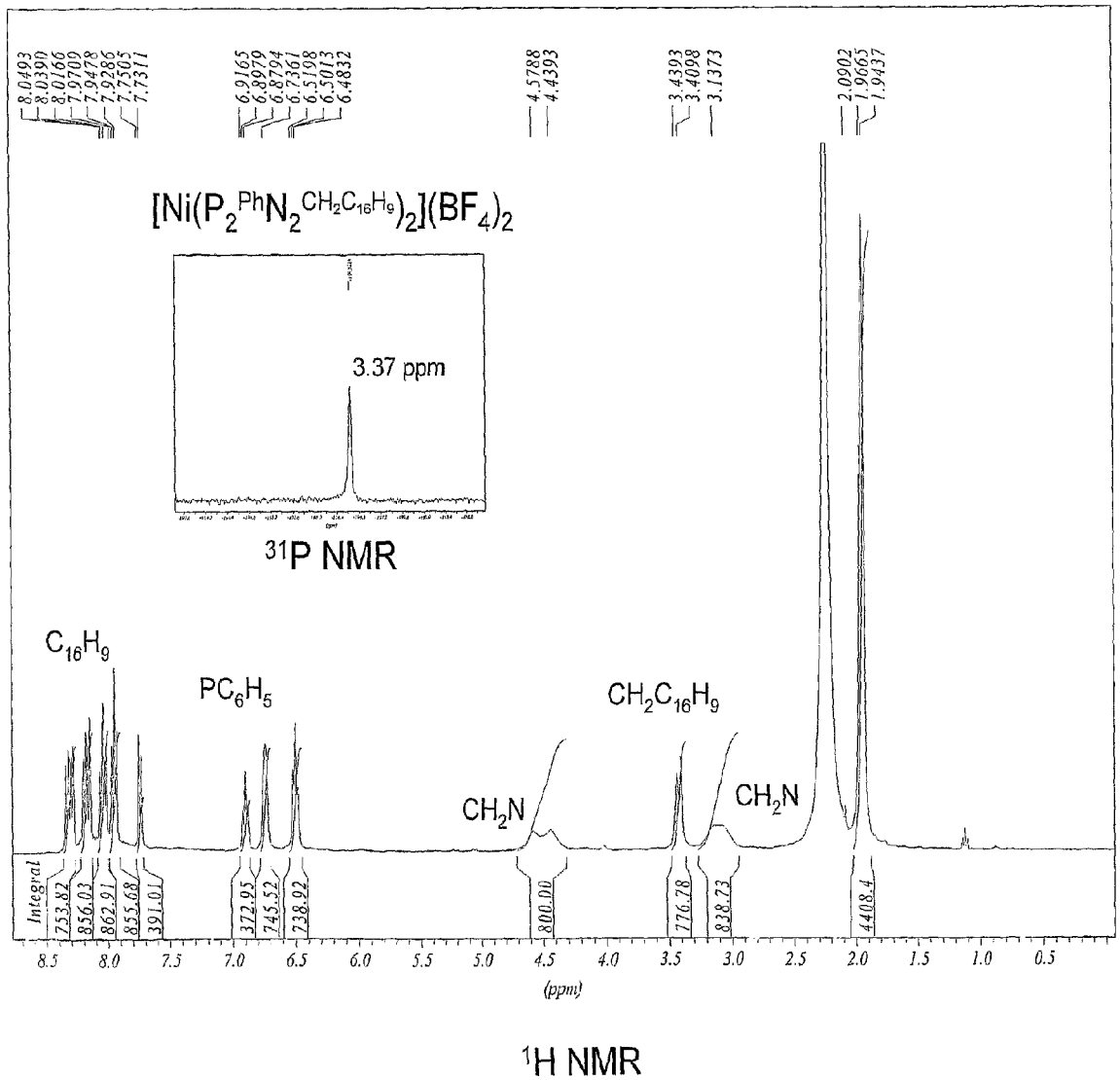

An activated ester $P_2^{Ph}N_2^R$ (R3=PhCH$_2$CH$_2$COOPht) was synthesized by coupling the carboxylic function in $P_2^{Ph}N_2^{R1}$ with N-Hydroxy-phtalimide in the presence of EDC. The synthesis of the nickel complexes [Ni($P_2^{Ph}N_2^R$)$_2$](BF$_4$)$_2$ (R=R2 and R3) was achieved by mixing 2 equivalents of the diphosphine ligand and a nickel(II) precursor in MeCN (FIG. 1—scheme 2). The ligands and the complexes were characterized by $^{31}$P NMR and $^1$H NMR. The chemical shifts of both complexes are similar to those obtained by DuBois and coll. (DuBois et al., J. Am. Chem. Soc. 2006, 128, 358) for [Ni($P_2^{Ph}N_2^{Ph}$)$_2$](BF$_4$)$_2$ (FIGS. 2 and 3).

Figure 4:
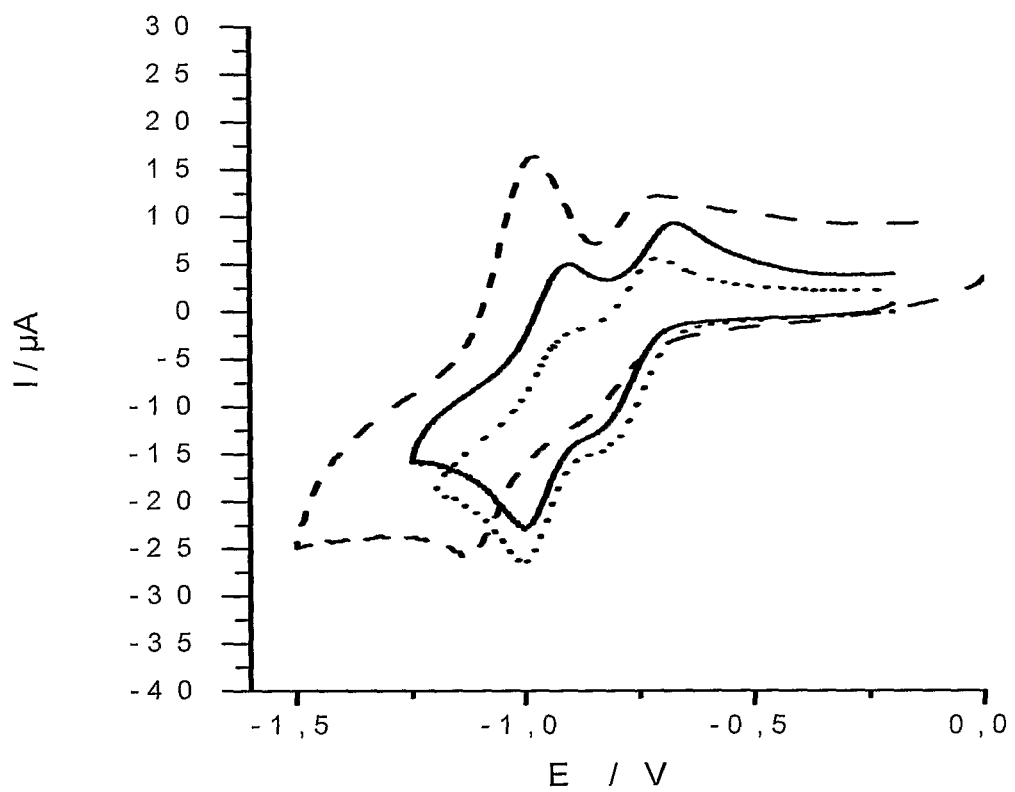

Two reversible reductions at $E_{1/2}^{red1}$=−0.75−−0.8 and $E_{1/2}^{red2}$=−0.95−−1.05 V vs Ag/AgClO$_4$, 0.01 mol.L$^{-1}$ (Table 1) were observed in MeCN at a glassy carbon electrode (FIG. 4). The first reduction exhibits a slow electron transfer compared to the second one. This is probably due to a ligand reorganization triggered by the first electron transfer slowing down the heterogeneous transfer rate.

TABLE 1

Redox potentials for the reduction processes of
[Ni($P_2^{Ph}N_2^R$)$_2$](BF$_4$)$_2$ in MeCN—Bu$_4$NPF$_6$ 0.2M (potentials are quoted versus the Ag/AgClO$_4$, 0.01 mol · L$^{-1}$ electrode)

| [Ni($P_2^{Ph}N_2^R$)$_2$](BF$_4$)$_2$ | $E_{1/2}^{red1}$ (V) | $E_{1/2}^{red2}$ (V) |
|---|---|---|
| R = Ph | −0.77 | −0.95 |
| R = PhCH$_2$CH$_2$COOPht | −0.76 | −0.95 |
| R = CH$_2$C$_{16}$H$_9$ | −0.80 | −1.05 |

Addition of acid to the electrochemical cell confirmed their electrocatalytic behavior towards the reduction of proton. At $E_p^{red}$=−0.5 V vs Ag/AgClO$_4$, 0.01 mol.L$^{-1}$, a reduction wave is detected, indicating the protonation of the Ni(II) complex. Electrocatalytic reduction was confirmed by cyclic voltammetry performed at different concentrations of acid [DMFH]OTf (FIG. 5). The linear dependence of the catalytic current with the number of added protons (FIG. 6) confirmed the electrocatalytic nature of the reduction process and showed that the modifications of the ligands did not affect the properties of the catalysts.

Amino-Functionnalized ITO/MWCNT and Graphite/MWCNT Electrodes

The ITO/MWCNT and graphite/MWCNT electrodes were made by deposition of a thin film of nanotubes on ITO or graphite with a soluble membrane technique. (Z. C. Wu et al., Science 2004, 305, 1273). These electrodes were modified by reduction of a diazonium salt (4-(2-Ammonioethyl)benzenediazonium tetrafluoroborate) at the ITO/MWCNT or graphite/MWCNT working electrode. Cyclic voltammetry was used to control the reduction of the diazonium salt. An irreversible reduction is observed at $E_p^{red}$=−0.26 V vs Ag/AgClO$_4$, 0.01 mol.L$^{-1}$, corresponding to the reduction of 2-aminoethylbenzenediazonium and the grafting of the polyphenylene layer on the CNT electrode. Several scans were performed to warrant a good functionalization of the CNTs. On the second and third scan, a deviation of the reduction peak to more negative potentials indicate an increasing thickness of the polyphenylene layer but a conserved fast electron transfer. Different conditions were studied by controlled potential electrolysis to maximize the quantity of amine groups at the electrode surface. The reversible reduction system of the immobilized nickel complex (see below) was used as a redox probe to determine the best conditions for obtaining high surface concentrations of the catalyst.

Figure 7:
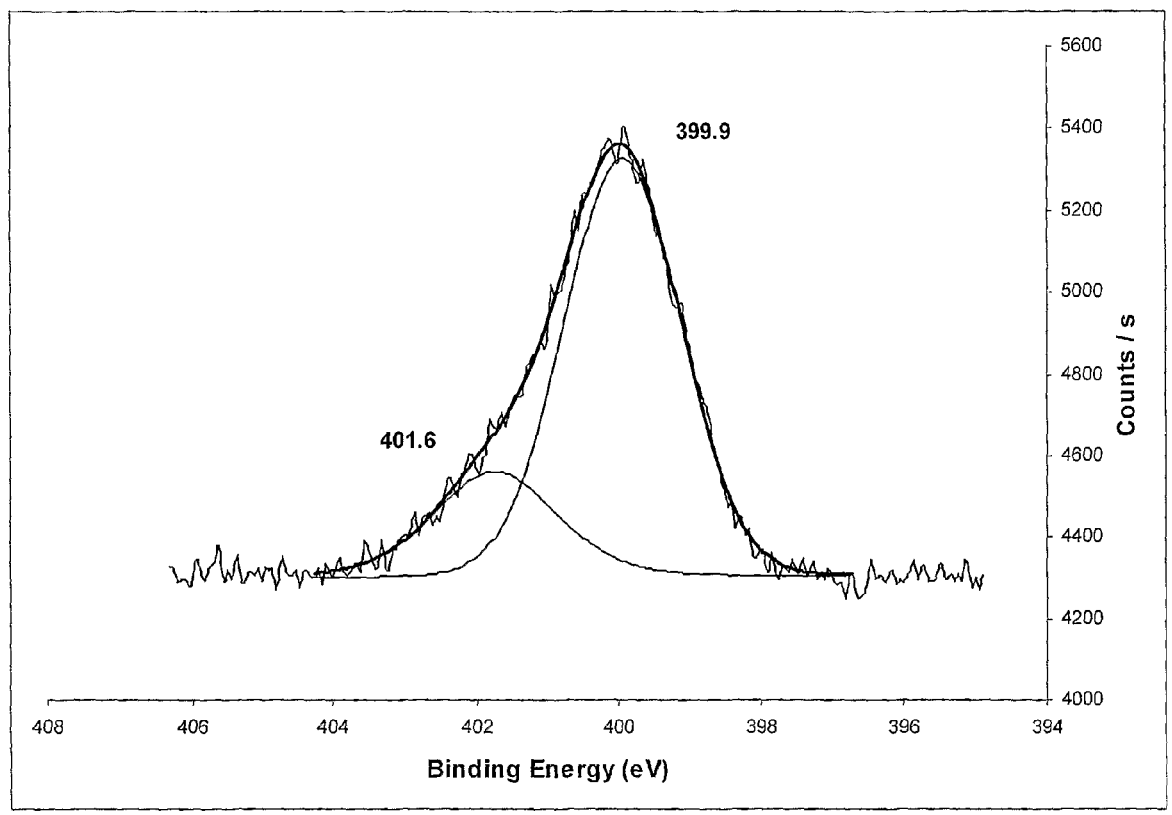
Figure 8:
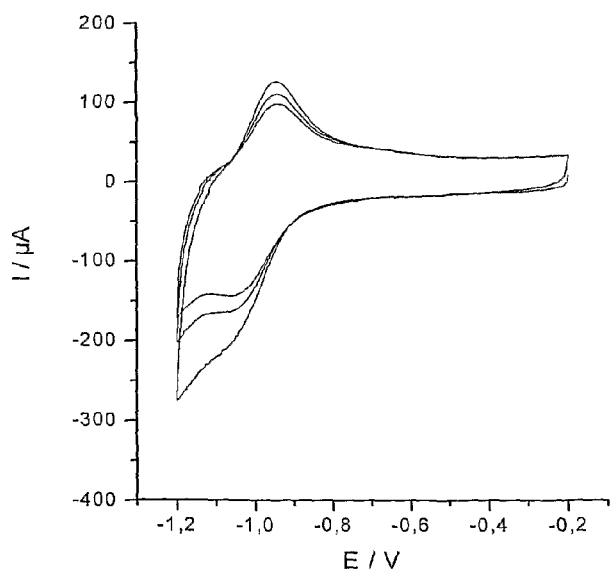

The functionalized CNT surface was further characterized by XPS measurement. XPS spectrum of the energy of 1s orbitals of N atom exhibits two peaks at 399.9 and 401.6 eV, indicating the presence of both amine and ammonium groups. (FIG. 7)

Immobilization Step of the Modified Nickel Catalysts

An heterogeneous amidification reaction was realized between functionalized electrodes and nickel complexes [Ni($P_2^{Ph}N_2^{R3}$)$_2$](BF$_4$)$_2$ bearing an activated ester group. The amine-functionalized electrodes were dipped in a solution of [Ni($P_2^{Ph}N_2^R$)$_2$](BF$_4$)$_2$ in the presence of triethylamine. The solution was stirred overnight. The covalent grafting of the complex was confirmed by cyclic voltammetry (FIG. 8) and XPS measurements (FIG. 9). The structure of the final electrode material is represented in FIG. 13A The XPS spectrum (FIG. 9) exhibits a clear Ni $2p_{1/2}$ and $2p_{3/2}$ signal corresponding to nickel atoms in a high oxidation state.

Cyclic voltammetry (FIG. 8) confirms the presence of the nickel covalently grafted to the electrode. A reduction at $E_{1/2}^{red}$=−0.95V (ΔE=140 mV) is observed, corresponding to the second reduction of the complex in solution. Resistivity due to the polyphenylene layer prevents from distinguishing the first slow electron transfer and the first reduction is not clearly detected. Considering the planar area of the electrode, the surface concentration of the nickel complex was estimated from the charge quantity calculated from the integration of the oxidation or reduction wave. Average concentrations were of an order of 10$^{-9}$ mol.cm$^{-2}$. The high surface area of the electrode was confirmed by the MEB image of these nanostructured electrodes (FIGS. 17A and 17B).

Electrocatalytic Properties of Functionnalized Nanostructured Electrodes

When [DMFH](OTf) was added as the proton source, a reduction peak appeared at a potential that is 300 mV more negative as compared to that achieved in the absence of acid and corresponding to the reduction of the protonated immobilized Ni(II) complex.

When the concentration of acid was increased, the peak current increased proportionally (FIG. 10). A supported electrocatalytic behaviour is doubtlessly evidenced by the trace of the catalytic current at different concentrations of acid (FIG. 11).

Electrolysis experiments were performed to investigate the stability of the covalent linkage and the effective production of H$_2$. Electrolysis was performed at a potential of −0.5V vs Ag/AgCl in an electrochemical cell coupled to a GC chromatographer. The catalyst activity is stable for hours. A charge current decrease is observed on a long time experiment for ITO/MWCNT electrodes that is due to the degradation of the CNT-ITO interface. This degradation does not happen for graphite/MWCNT based electrodes. 0.3 mL of H$_2$ were produced and characterized by GC in 1 h (FIG. 12, see the experimental section). Taking into account a blank experiment in order to subtract residual current passing through the cathode under the same conditions but in the absence of the grafted nickel catalyst this correspond to the passage of 3 C. Considering the surface concentration of the catalysts, turnover numbers were estimated to be 15000 within a 1 hour experiment corresponding to turnover-frequencies of 6 s$^{-1}$. The production of H$_2$ thus proved to be highly efficient. By comparison, the nickel complexes in solution were only shown to achieve 7 turnovers under similar bulk electrolysis conditions (DuBois et al., J. Am. Chem. Soc. 2006, 128, 358)

It is noteworthy that catalytic behaviour for pristine and amino-functionalized CNTs was observed at −1.2V, i.e. 500 mV more negative than the nickel-functionalized-MWCNT. This study implicates the great importance of the presence of catalyst at the surface of the electrode so that hydrogen can be produced at low overpotentials.

Practical applications of such molecular electrode materials require that they can be used with aqueous electrolytes.

FIG. 19 illustrates results obtained from rotating ring-disk electrode measurements (5 mV.s$^{-1}$) for hydrogen evolution from 0.5 M $H_2SO_4$ aqueous solution on MWCNTS and Ni-functionalized MWCNTs. The material is deposited as a Nafion based ink on the GC disk. A Top: disk potential; middle: disk current density (pristine MWCNTS (a) and Ni-functionalized MWCNTs (b); bottom: Pt-ring current for both samples—The Pt-ring is poised at 0.6 V. B. Evolution of current density as a function of the potential for both hydrogen production and oxidation from 0.5 M $H_2SO_4$ aqueous solution recorded at a MEA consisting of a gas diffusion layer (GDL) assembled with a Nafion membrane (2 mV.s$^{-1}$): (a) unfunctionalized GDL; (b) Ni-functionalized GDL under an atmosphere of $N_2$; (c) Ni-functionalized GDL under an atmosphere of $H_2$ ($10^5$ Pa). The x-axis is positioned at zero current density. Dots represent stabilized values of current at electrodes set for 10 minutes at various potentials. C. logarithmic plots of current density as a function of the potential for both hydrogen production and uptake corresponding to traces (a) and (c) shown in C; (d): same measurement on a commercial MEA containing highly dispersed platinum (0.5 $mg_{Pt}$.cm$^{-2}$). Potential are quoted versus NHE.

Catalytic hydrogen production from diluted pH 1 sulphuric acid solutions has been demonstrated in two ways. First, we used a glassy carbon-disc electrode covered by a small amount of powder of Ni-functionalized MWCNTs dispersed in a 5 wt % Nafion® solution. Rotating electrode measurements (FIG. 19A) confirm that $H_2$ can be produced on the disc electrode and simultaneously detected at a concentric platinum ring poised at 0.6 V vs NHE. The analysis of the voltammograms reveals that electrocatalytic hydrogen evolution occurs with an overvoltage of 20 mV, remarkably lower than that observed on pristine MWCNTs (128 mV). Second, our material has been assayed in a half-cell configuration reproducing the experimental conditions found in state to the art proton-exchange membrane electrolysers and in which the platinum-based active layer is replaced by Ni-functionalized MWCNTs. A membrane-electrode assembly (MEA) has been prepared for that purpose: it consists of a Nafion® membrane hot-pressed with a gas diffusion layer (GDL) on which the MWCNTs have been deposited and further functionalized with the nickel diphosphine catalyst using the diazonium route. This MEA displays an electrocatalytic activity for hydrogen evolution significantly superior to that of unfunctionalized GDL or amino-functionalized MWNTCs under similar conditions (FIG. 19C). Importantly, no rapid evolution of the material is observed under these conditions since the stabilized current values measured at a MEA set for 10 min at various potentials nicely fit with those of the initial voltammogram. This allows to preclude the formation of nickel-based particles as the catalytically active species. In any case, from the Pourbaix diagram, either nickel oxide/hydroxide compounds or elemental nickel would be unstable under the assay conditions. This membrane-electrode assembly (MEA) was poised at −300 mV vs NHE in 0.5 M $H_2SO_4$ for 10 hours. Hydrogen evolution, monitored during the first half-hour using gas chromatography, corresponds to 3500 turnovers per catalytic centre, with a quantitative faradaic yield. The current density keeps constant over the all experiment, with more than 100.000 turnovers achieved (FIG. 20).

FIG. 20 illustrates the long-run electrolysis experiments for both hydrogen evolution and oxidation carried out respectively at −0.3 and +0.3 V vs NHE in $H_2SO_4$ (0.5 mol.L$^{-1}$) on a membrane electrode assembly functionalized with the nickel catalyst via the diazonium route.

The unexpectedly low overvoltage observed here for hydrogen production let us consider this material for the reverse reaction, ie catalytic hydrogen oxidation. The same membrane-electrode assembly has then been assayed under the same conditions as described above except that a hydrogen atmosphere was used instead of nitrogen. The corresponding voltammogram is shown in FIG. 19C. The cathodic part—hydrogen production—is almost unchanged. The material clearly catalyzes catalytic hydrogen oxidation with a current density of about 2 mA.cm$^{-2}$ at 500 mV overvoltage, twice the value measured for hydrogenases adsorbed on graphite electrodes (M. Hamburger et al., J. Am. Chem. Soc. 130, 2015 (2008). or covalently immobilized onto MWCNT electrodes (M. A. Alonso-Lomillo et al., Nano Lett. 7, 1603 (2007)). The catalytic current is stable during a 10 h-electrolysis experiment corresponding to the achievement of ~35.000 turnovers (FIG. 20). The shape of the voltammogram indicates a kinetic limitation due to the diffusion of hydrogen at the grafted active sites. The same effect has been observed for immobilized hydrogenases (K. A. Vincent, A. Parkin, F. A. Armstrong, Chem. Rev. 107, 4366 (2007)). FIG. 19C shows a logarithmic representation of the voltammograms recorded under $H_2$ ($10^5$ Pa). The potential values corresponding to the severe deviations from linearity correspond to the overvoltage for $H^+/H_2$ interconversion and are clearly shown to be close to zero for the MEA containing the Ni-functionalized material. FIG. 19C also compares our MEA with a commercial MEA containing highly dispersed platinum (0.5 mg Pt.cm$^{-2}$) and exhibiting current density about two orders of magnitude higher.

Functionalization of GDL/MWCNT Electrodes Using Linker (IA)

The catalyst [Ni($P_2^{Ph}N_2^{CH2C16H19}$)$_2$](BF$_4$)$_2$ (see figure below) has been immobilized on a Gas diffusion Layer on which MWNTCs have been first deposited. The interaction of this linker corresponding to structure (IA) with the solid support, here MWCNTs, is exclusively via π-staking. The resulting electrode displayed a surface concentration of catalysts of 4 (±1.5) 10$^{-9}$ mol.cm$^{-2}$ as determined from electrochemical measurements.

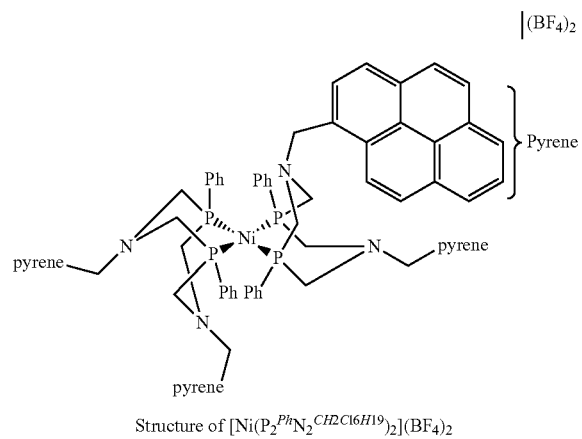

Structure of [Ni($P_2^{Ph}N_2^{CH2C16H19}$)$_2$](BF$_4$)$_2$

This electrode has then been assembled with a Nafion membrane and assayed under the same conditions. FIG. 21 shows the results that have been obtained, confirming the potential of this type of immobilization for sustaining the electrocatalytic activity for both hydrogen evolution and oxidation.

FIG. 21 illustrates evolution of current density as a function of the potential for both hydrogen evolution and oxidation from 0.5 M $H_2SO_4$ aqueous solution recorded at a MEA consisting of a gas diffusion layer (GDL) assembled with a Nafion membrane (2 $mV.S^{-1}$): grey, GDL with deposited MWNTCs ; solid line, GDL with deposited MWCNTs and further immobilization of $[Ni(P_2^{Ph} N_2^{CH2C16H19})_2](BF_4)_2$ under an atmosphere of $N_2$; dotted line, GDL with deposited MWCNTs and further immobilization of $[Ni (P_2^{Ph}N_2^{CH2C16H19})_2](BF_4)_2$ under an atmosphere of $H_2$. Potentials are quoted versus NHE.

To conclude, we have demonstrated here the possibility to implement a cheap and robust, air-stable bio-inspired mimic of the active site of hydrogenase enzymes into a noble-metal free electrocatalytic nanomaterial operating bidirectionally, ie for both sustained hydrogen evolution and uptake at low overvoltage. While its nominal and non-optimized performances remain two orders of magnitude lower in terms of current exchange density as compared to Pt-loaded (0.5 $mg.cm^{-2}$) carbon materials currently used in commercial fuel-cells, this is greatly balanced by the fact that the catalyst loading is actually limited to 0.06 $mg.cm^{-2}$ of an earth-abundant metal. Our results clearly show that the biomimetic nanomaterial reported here displays a unique stability upon cycling allowing tenths of thousand turnovers in short time and is compatible with the widespread PEM technology based on commercial proton exchange membranes and working in acidic conditions.

The invention claimed is:

1. A material comprising a solid support of a conductive or semi-conductive material which is functionalized on its surface by linker arms, said linker arms comprising at least two extremities, wherein the first extremity is bonded to the solid support and the second extremity is linked in a covalent manner to a metal-organic complex, wherein the linker arm is selected from molecules responding to the following formulae:

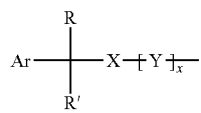
(IA)

in which case the interaction between the linker and the solid support is via π-stacking, and to oligomers resulting from the oligomerization of:

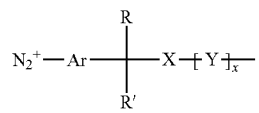
(IC)

in which case the linker is covalently linked through the Ar group to the solid support,
wherein:
Ar represents a $C_6$-$C_{30}$ aromatic residue, possibly comprising one or more substituents selected from: $C_1$-$C_6$ alkyl, —OH, —$NH_2$, —COOH, —F, —Cl, —Br, —I, —$NO_2$, —$CONR''_2$, —$COOR''$, —$SO_3^-$, —$SR''$, —$OR''$, —$NR''_2$;
R and R', identical or different, represent a group selected from: H, $C_1$-$C_{20}$ alkyl, $C_1$-$C_{20}$ alkenyl, $C_1$-$C_{20}$ alkynyl, $C_6$-$C_{30}$ aryl, $C_6$-$C_{30}$ aralkyl, possibly comprising one or more substituents selected from: —OH, —$NH_2$, —COOH, —$CONH_2$, triazole, —SH, —$N_3$, and optionally interrupted by one or more bridges selected from: —CONH—, —CO—O—, —CO—O—CO—, —CO—NH—CO—, —CO—S—, —CS—O—, and —CS—S—;

R" represents a group selected from: H, $C_1$-$C_{20}$ alkyl, $C_1$-$C_{20}$ alkenyl, $C_1$-$C_{20}$ alkynyl, $C_6$-$C_{30}$ aryl, and $C_6$-$C_{30}$ aralkyl;

X represents a group selected from: $C_1$-$C_{20}$ alkyl, $C_1$-$C_{20}$ alkenyl, $C_1$-$C_{20}$ alkynyl, $C_6$-$C_{30}$ aryl, $C_6$-$C_{30}$ aralkyl, and optionally comprising one or more substituents selected from: —OH,—$NH_2$, —COOH, —$CONH_2$, triazole, —SH, —$N_3$, and optionally interrupted by one or more bridges selected from: —CONH—, —CO—O—, —CO—O—CO—, —CO—NH—CO—, —CO—S—, —CS—O—, —CS—S—;

x is an integer, 1≤x≤5;

Y is a functional group selected from: a simple covalent link, —O—, —NH—, —S—, —COO—,—CONH, —CO—S—, —CS—O—, and —CS—S—, and wherein the metal-organic complex is selected from those responding to the following formula:

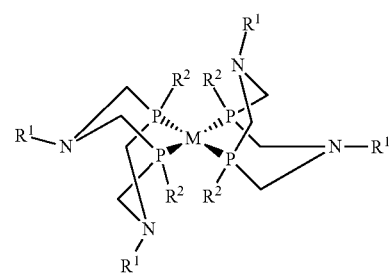

wherein

M represents an atom selected from transition metals of the periodic table of elements, and $R_1$, $R_2$, identical or different, represent a group selected from: H, $C_1$-$C_{20}$ alkyl, $C_1$-$C_{20}$ alkenyl, $C_1$-$C_{20}$ alkynyl, $C_6$-$C_{30}$ aryl, $C_6$-$C_{30}$ aralkyl, optionally comprising one or more functions selected from: —OH, —$NH_2$, —COOH , —$CONH_2$, a triazole ring, optionally comprising one or more bridges selected from: —CO—O—CO—, —CO—NH—CO—and at least one of the $R_1$ groups or one of the $R_2$ groups represents a covalent link with the linker molecule, two or more $R_1$ substituents can be fused together, two or more $R_2$ substituents can be fused together.

2. A material according to claim 1, wherein the solid support is selected from: a metallic material, a carbon material, a semi-conductor or conductor metal oxide, nitride, and chalcogenide.

3. A material according to claim 2, wherein the solid support is selected from multi-wall carbon nanotubes.

4. A material according to claim 1, wherein the linker arm results from the oligomerization of

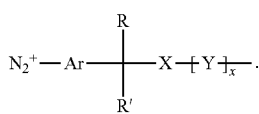 (IC)

5. A material according to claim 1, wherein in the formulae (IA) and (IC):
Ar represents a $C_6$-$C_{30}$ aromatic residue selected from: phenyl, biphenyl, pyrenyl, anthracenyl, phenanthrenyl, perylenyl, and naphtacenyl,
R and R' represent a group selected from: H, $C_1$-$C_{20}$ alkyl, $C_1$-$C_{20}$ alkenyl, $C_1$-$C_{20}$ alkynyl, $C_6$-$C_{30}$ aryl, $C_6$-$C_{30}$ aralkyl, and R=R'=H,
X represents a group selected from: $C_1$-$C_{20}$ alkyl, $C_1$-$C_{20}$ alkenyl, $C_1$-$C_{20}$ alkynyl, $C_6$-$C_{30}$ aryl, and $C_6$-$C_{30}$ aralkyl,
x=1.

6. A material according to claim 1, wherein the metal-organic complex, when studied in solution, displays electrocatalytic activity for hydrogen evolution or uptake.

7. A material according to claim 1, wherein all the $R_1$ groups are identical with the possible exception of at least one $R_1$ group which is a covalent link with the linker molecule and all the $R_2$ are identical with the possible exception of at least one $R_2$ group which is a covalent link with the linker molecule.

8. A material according to claim 1, wherein M is selected from the group consisting of: Mn, Fe, Co, Ni, W, and Mo.

9. An electrode comprising a material according to claim 1 deposited on a support of another conductive material.

10. An electrode according to claim 9, wherein the other conductive material is selected from: indium tin oxide (ITO) and graphite.

11. An electrode according to claim 10, which responds to the following formula:

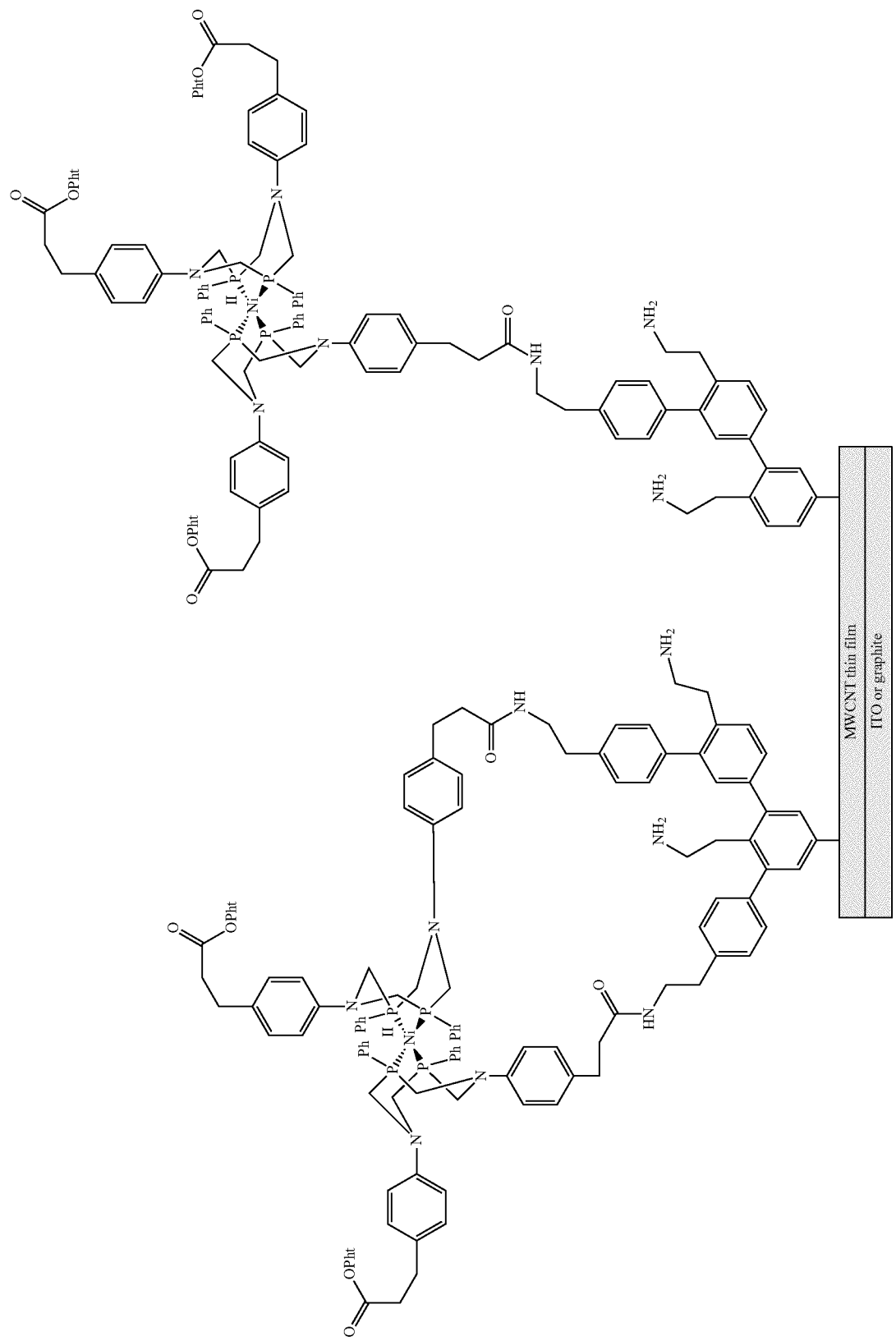

12. An electrode according to claim 9, which responds to the following formula:
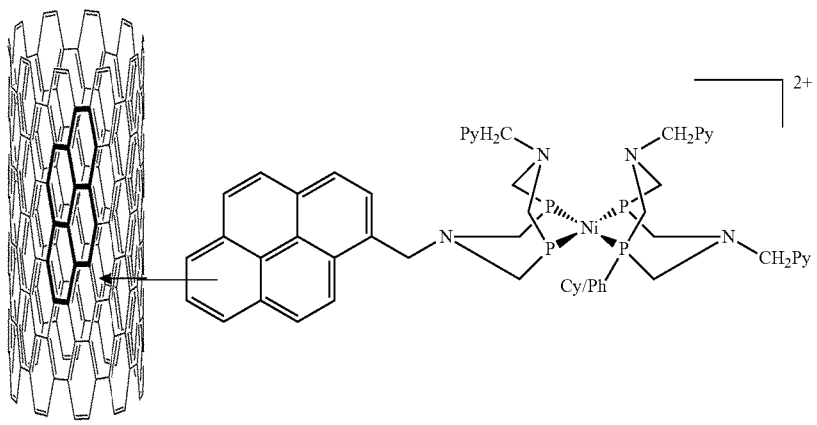
13. A water electrolyser comprising an electrode according to claim 9.
14. A fuel cell comprising an electrode according to claim 9.
* * * * *

UNITED STATES PATENT AND TRADEMARK OFFICE
CERTIFICATE OF CORRECTION

| | | |
|---|---|---|
| PATENT NO. | : 8,895,207 B2 | Page 1 of 1 |
| APPLICATION NO. | : 13/125210 | |
| DATED | : November 25, 2014 | |
| INVENTOR(S) | : Artero et al. | |

It is certified that error appears in the above-identified patent and that said Letters Patent is hereby corrected as shown below:

<u>Title page,</u>
Item (75) Inventors: "Chartruse (FR)" should read --Chartreuse (FR)--.

Signed and Sealed this
Fourteenth Day of April, 2015

Michelle K. Lee
*Director of the United States Patent and Trademark Office*